(12) United States Patent
Niklason et al.

(10) Patent No.: US 10,772,938 B2
(45) Date of Patent: Sep. 15, 2020

(54) COMPOSITIONS AND METHODS OF INCREASING LONGEVITY OR TREATING CELLULAR STRESS

(71) Applicant: YALE UNIVERSITY, New Haven, CT (US)

(72) Inventors: Laura E. Niklason, Greenwich, CT (US); Xiangru Xu, Cheshire, CT (US); Hong Qian, Cheshire, CT (US)

(73) Assignee: Yale University, New Haven, CT (US)

( * ) Notice: Subject to any disclaimer, the term of this patent is extended or adjusted under 35 U.S.C. 154(b) by 265 days.

(21) Appl. No.: 15/543,367

(22) PCT Filed: Jan. 13, 2016

(86) PCT No.: PCT/US2016/013220
§ 371 (c)(1),
(2) Date: Jul. 13, 2017

(87) PCT Pub. No.: WO2016/115233
PCT Pub. Date: Jul. 21, 2016

(65) Prior Publication Data
US 2018/0008679 A1    Jan. 11, 2018

Related U.S. Application Data

(60) Provisional application No. 62/197,613, filed on Jul. 28, 2015, provisional application No. 62/102,751, filed on Jan. 13, 2015.

(51) Int. Cl.
*A61K 38/45*       (2006.01)
*A61K 31/7088*     (2006.01)
*C12N 15/113*      (2010.01)
*C12N 9/12*        (2006.01)
*A61K 38/17*       (2006.01)

(52) U.S. Cl.
CPC .......... *A61K 38/45* (2013.01); *A61K 31/7088* (2013.01); *A61K 38/1709* (2013.01); *C12N 9/12* (2013.01); *C12Y 207/11024* (2013.01)

(58) Field of Classification Search
None
See application file for complete search history.

(56) References Cited

U.S. PATENT DOCUMENTS

2010/0173024 A1   7/2010   McDaniel

FOREIGN PATENT DOCUMENTS

WO      9905278 A1    2/1999

OTHER PUBLICATIONS

International Search Report and Written Opinion for PCT International Application No. PCT/US2016/013220 dated May 23, 2016.

Banerjee, et al., "TRIP13 promotes error-prone nonhomologous end joining and induces chemoresistance in head and neck cancer", Nat Commun. 5, 2014, 4771.
Bhalla, et al., "A conserved checkpoint monitors meiotic chromosome synapsis in Caenorhabditis elegans", Science. 310(5754), 2005, 1683-1686.
Bishop, et al., "The Caenorhabditis elegans Aurora B kinase AIR-2 phosphorylates and is required for the localization of a BimC kinesin to meiotic and mitotic spindles", Mol Biol Cell. 16(2), 2005, 742-756.
Bolcun-Filas, et al., "Reversal of female infertility by Chk2 ablation reveals the oocyte DNA damage checkpoint pathway", Science. 343(6170), 2014, 533-536.
Civelekoglu-Scholey G, et al., "Mitotic motors: kinesin-5 takes a brake", Curr Biol. 17(14), 2007, R544-547.
Deshong, et al., "A quality control mechanism coordinates meiotic prophase events to promote crossover assurance", PLoS Genet. 10(4), 2014, e1004291.
Fargnoli, et al., "Decreased expression of heat shock protein 70 mRNA and protein after heat treatment in cells of aged rats", Proc Natl Acad Sci U S A. 87(2), 1990, 846-850.
Fawcett, "Effects of neurohormonal stress and aging on the activation of mammalian heat shock factor 1", J Biol Chem. 269(51), 1994, 32272-32278.
Fontana, et al., "Dietary Restriction, Growth Factors and Aging: from yeast to humans", Science. 328(5976), 2010, 321-326.
Garrido, et al., "HSP27 and HSP70: potentially oncogenic apoptosis inhibitors", Cell Cycle. 2(6), 2003, 579-584.
Hirokawa, et al., "Kinesin superfamily proteins (KIFs): Various functions and their relevance for important phenomena in life and diseases", Exp Cell Res. 334(1), 2015, 16-25 (Abstract Only).
Kenyon, "The genetics of ageing", Nature. 464(7288), 2010, 504-512.
Kuningas, et al., "Genes encoding longevity: from model organisms to humans", Aging Cell. 7(2), 2008, 270-280.
Liu, et al., "Inhibition of the mitotic kinesin Eg5 up-regulates Hsp70 through the phosphatidylinositol 3-kinase/Akt pathway in multiple myeloma cells", J Biol Chem. 281(26), 2006, 18090-18097.
Miki, et al., "Analysis of the kinesin superfamily: insights into structure and function", Trends Cell Biol. 15(9), 2005, 467-476.
Morley, et al., "Regulation of longevity in Caenorhabditis elegans by heat shock factor and molecular chaperones", Mol Biol Cell. 15(2), 2004, 657-664.
Nakai, et al., "K858, a novel inhibitor of mitotic kinesin Eg5 and antitumor agent, induces cell death in cancer cells", Cancer Res. 69(9), 2009, 3901-3909.

(Continued)

*Primary Examiner* — Michelle F. Paguio Frising
(74) *Attorney, Agent, or Firm* — Saul Ewing Arnstein & Lehr LLP; Kathryn Doyle

(57) ABSTRACT

The present invention includes methods and compositions for increasing longevity of a cell and increasing cellular resistance to stress. In certain embodiments, the invention includes a method to induce gene expression of a homolog of Pachytene Checkpoint 2 (pch-2) or bmk-1 gene. The present invention also includes methods to treat oxidative stress or induce cellular death or apoptosis by administering a composition comprising a modulator of pch-2 or bmk-1 homolog gene expression.

10 Claims, 29 Drawing Sheets

Specification includes a Sequence Listing.

(56) References Cited

OTHER PUBLICATIONS

Qian, et al., "Bmk-1 regulates lifespan in Caenorhabditis elegans by activating hsp-16", Oncotarget. 6(22), 2015, 18790-18799.
Qian, et al., "PCH-2 regulates Caenorhabditis elegans lifespan", Aging (Albany NY). 7(1), 2015, 1-13.
Roig, et al., "Mouse TRIP13/PCH2 is required for recombination and normal higher-order chromosome structure during meiosis", PLoS Genet. 6(8), 2010, e1001062.
San-Segundo, et al., "Role for the silencing protein Dot1 in meiotic checkpoint control", Mol Biol Cell. 11(10), 2000, 3601-3615.
Sidler, et al., "Immunosenescence is associated with altered gene expression and epigenetic regulation in primary and secondary immune organs", Front Genet. 4(211), 2013, 1-16.
Sutphin, et al., "Measuring Caenorhabditis elegans life span on solid media", J Vis Exp. 27, 2009, 1152.
Tao, et al., "An inhibitor of the kinesin spindle protein activates the intrinsic apoptotic pathway independently of p53 and de novo protein synthesis", Mol Cell Biol. 27(2), 2007, 689-698.
Zhu, et al., "Silencing heat shock protein 27 decreases metastatic behavior of human head and neck squamous cell cancer cells in vitro", Mol Pharm. 7(4), 2010, 1283-1290.

Figure 1A

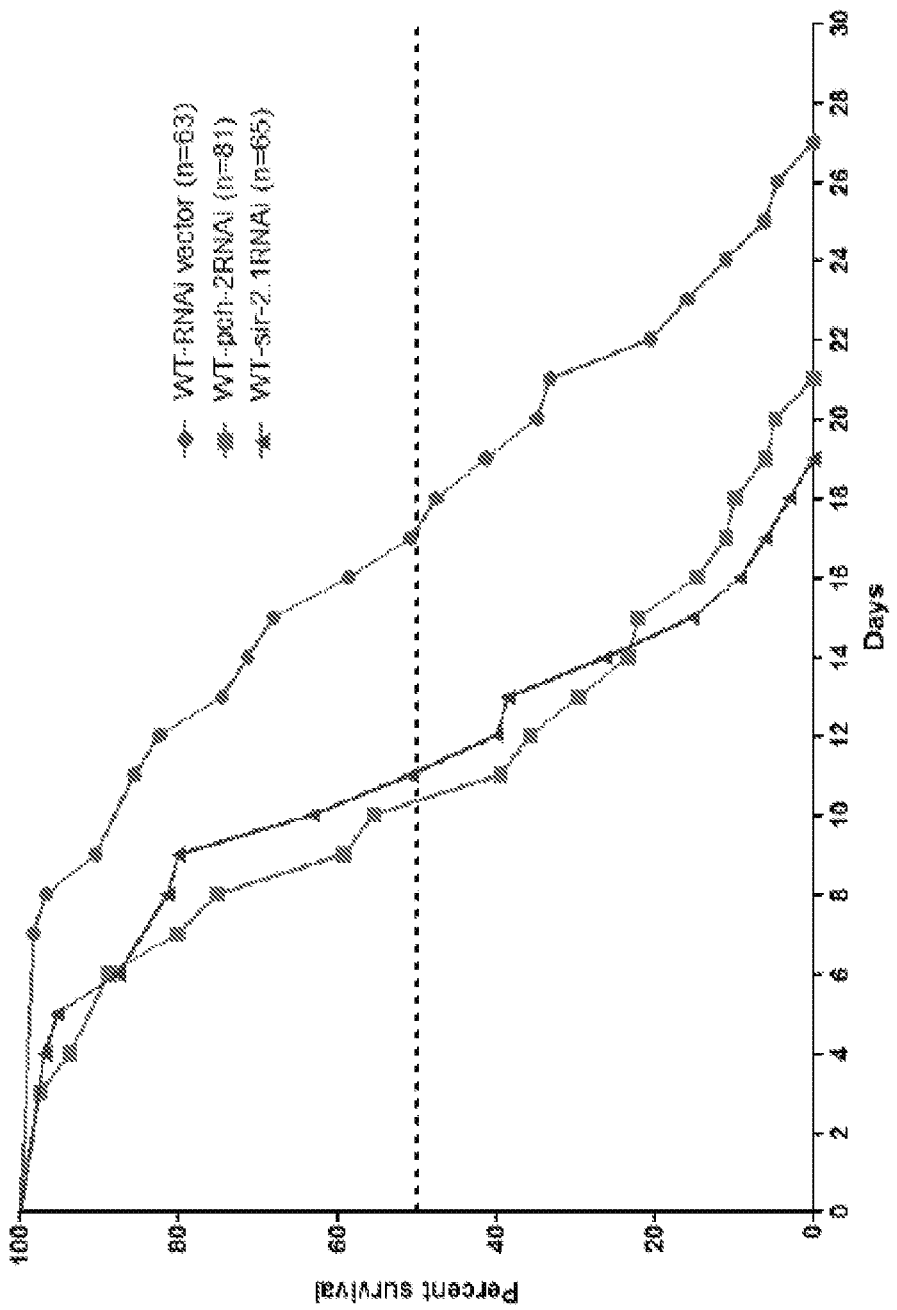

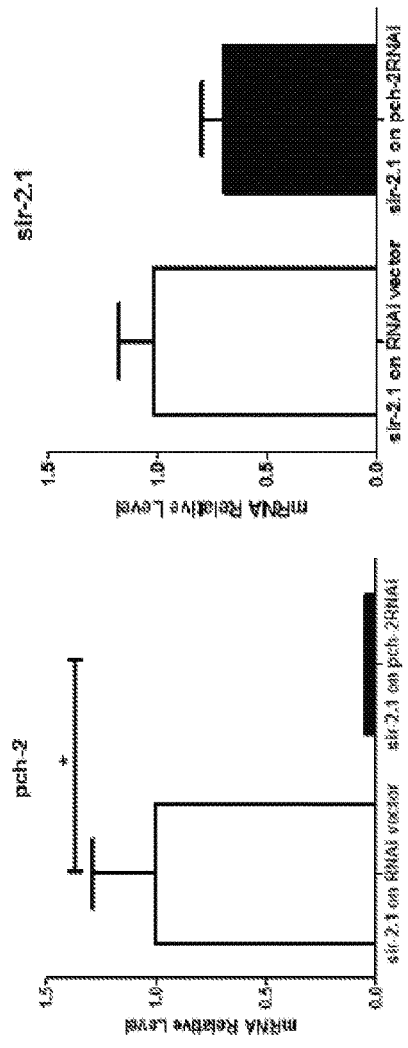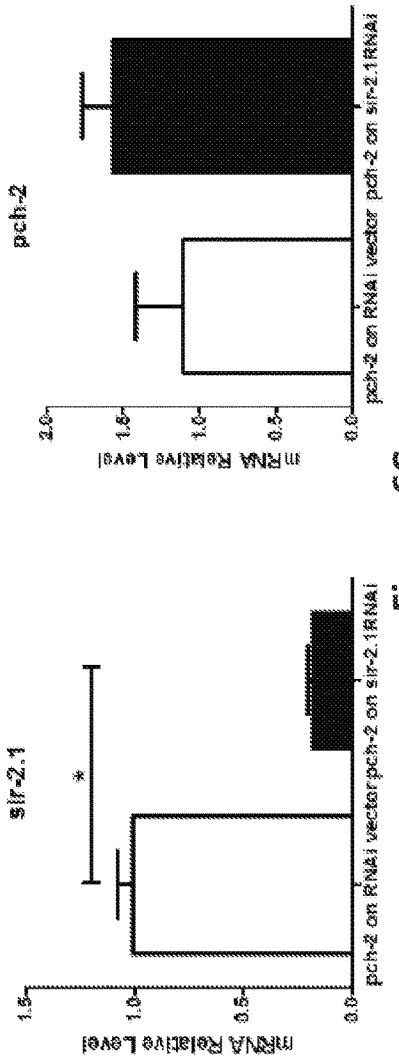
Figure 6B
Figure 6C

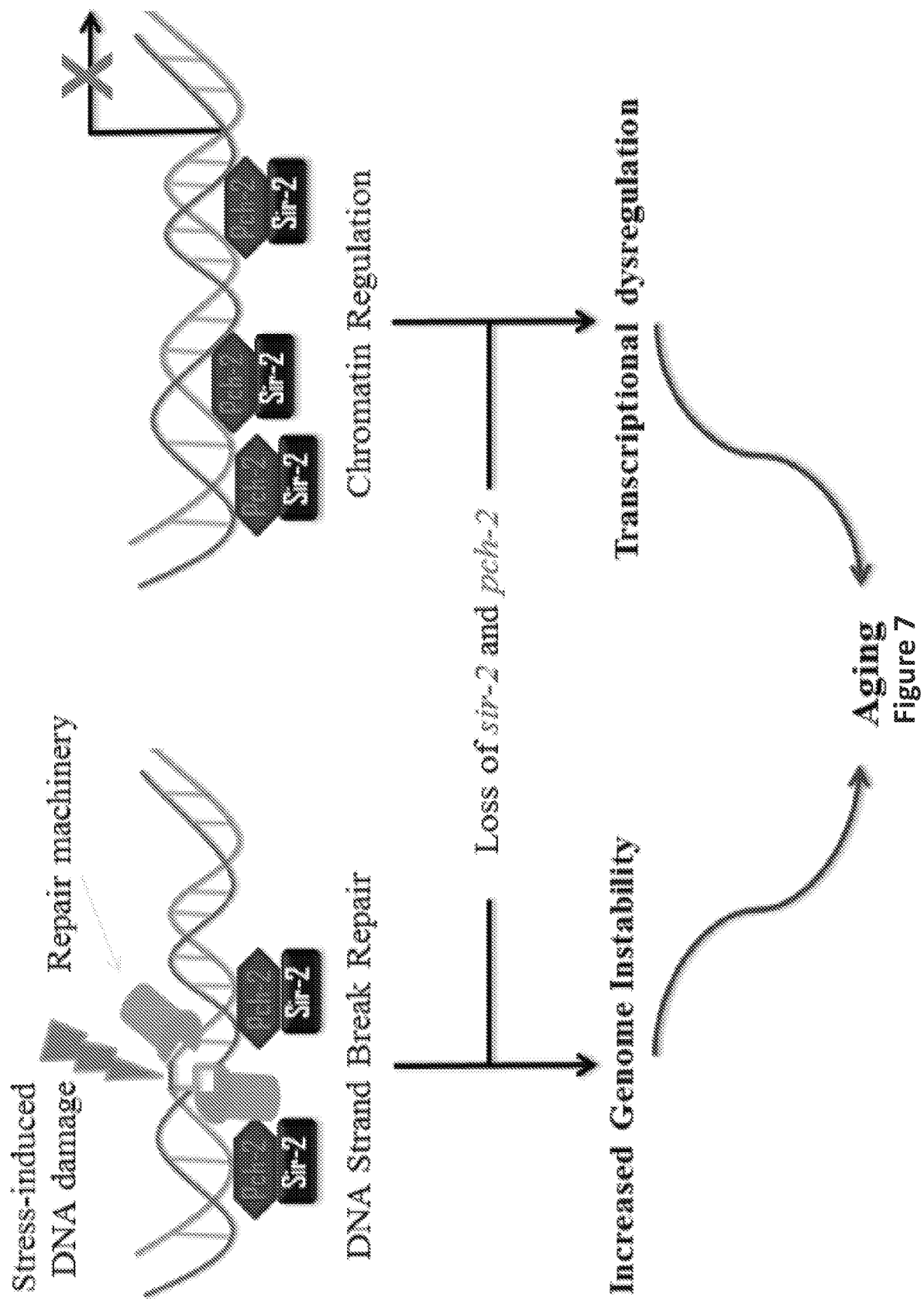

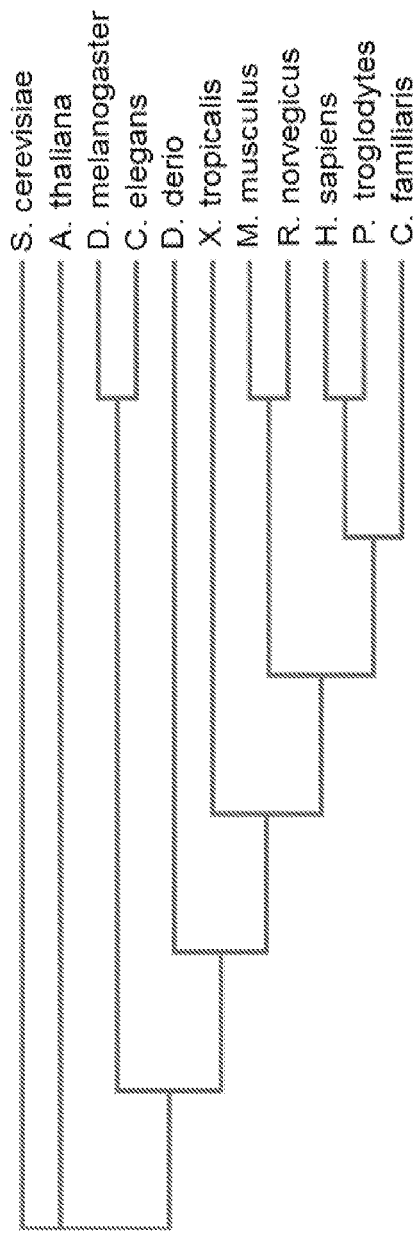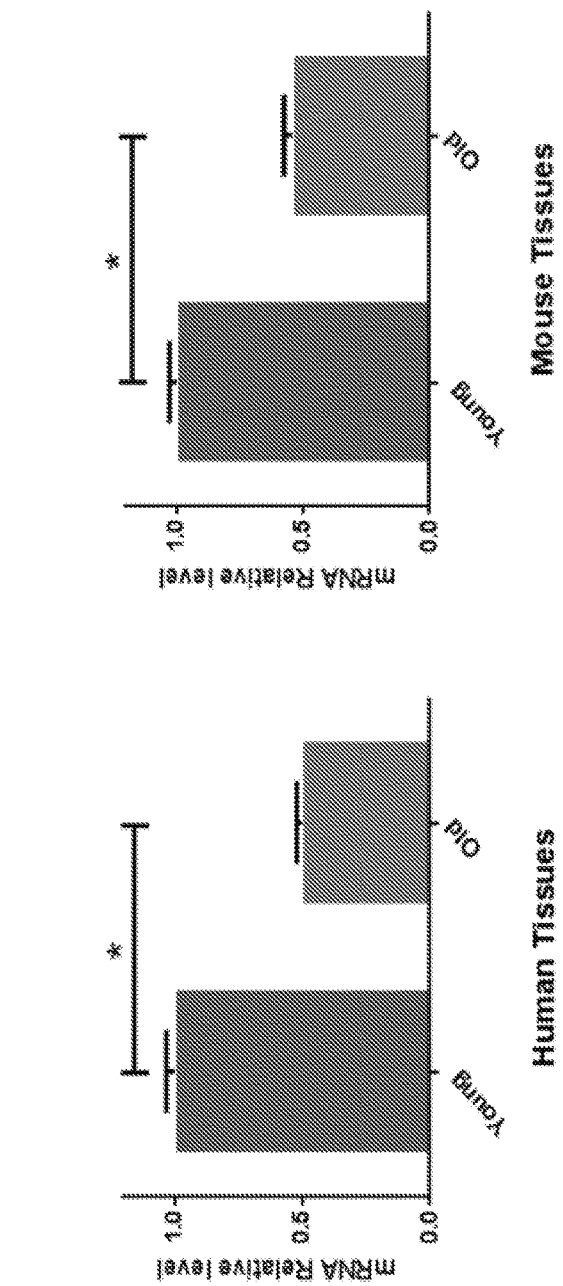
Figure 10

COMPOSITIONS AND METHODS OF INCREASING LONGEVITY OR TREATING CELLULAR STRESS

CROSS REFERENCE TO RELATED APPLICATION

This application is a 35 U.S.C. § 371 national phase application from, and claims priority to, International Application No. PCT/US2016/013220, filed Jan. 13, 2016, and published under PCT Article 21(2) in English, which claims priority under 35 U.S.C. § 119(e) to U.S. Provisional Pat. App. Ser. No. 62/102,751, filed Jan. 13, 2015, and U.S. Provisional Pat. App. Ser. No. 62/197,613, filed Jul. 28, 2015, all of which applications are incorporated herein by reference in their entireties.

BACKGROUND OF THE INVENTION

Based on the observation that maximum life span is species specific, it has been postulated that a gene network exists to determine the life span of a species. Very few people live to be older than one hundred and ten years old. Incredibly, many of these "supercentenarians" do virtually nothing to stay healthy or fit, leading scientists to speculate that certain genes are responsible. But recent analysis of the human genome suggests this is an oversimplification.

The genetic underpinnings of aging are far more complex. The action of a single gene can have huge effects on how long a creature lives. Even with many things determining life span, including a host of lifestyle factors and a long list of diseases, remarkable effects on life span are seen when particular genes are deleted from an animal's genetic sequence.

Thus, there is a need in the art for a better understanding of anti-aging genes and their use in treating the effects of aging. The present invention satisfies this unmet need.

SUMMARY OF THE INVENTION

In one aspect, the invention includes a method for increasing longevity of a cell or organism comprising administering to the cell or organism a composition to induce a homolog selected from the group consisting of Pachytene Checkpoint 2 (PCH-2) and BMK-1.

In another aspect, the invention includes a method for increasing cellular resistance to stress, aging or DNA damage in a cell comprising contacting the cell with a composition to induce a homolog selected from the group consisting of Pachytene Checkpoint 2 (PCH-2) and BMK-1.

In yet another aspect, the invention includes a method for increasing longevity of a cell or organism comprising administering a composition comprising a homolog selected from the group consisting of Pachytene Checkpoint 2 (PCH-2) and BMK-1.

In still another aspect, the invention includes a method for increasing cellular resistance to stress, aging or DNA damage in a cell comprising contacting the cell with a composition comprising a homolog selected from the group consisting of Pachytene Checkpoint 2 (PCH-2) and BMK-1.

In another aspect, the invention includes a method of treating a condition associated with oxidative stress, aging or DNA damage in a subject, comprising administering to the subject a therapeutically effective amount of a pharmaceutical composition comprising a nucleic acid encoding a homolog selected from the group consisting of Pachytene Checkpoint 2 (PCH-2) and BMK-1.

In still another aspect, the invention includes a method of treating a condition associated with oxidative stress, aging or DNA damage in a subject, comprising administering to the subject a therapeutically effective amount of a pharmaceutical composition comprising a modulator of a homolog selected from the group consisting of Pachytene Checkpoint 2 (PCH-2) and BMK-1.

In another aspect, the invention includes a method of treating a condition associated with oxidative stress, aging or DNA damage in a subject, comprising administering to the subject a therapeutically effective amount of a pharmaceutical composition comprising a homolog selected from the group consisting of Pachytene Checkpoint 2 (PCH-2) and BMK-1.

In yet another aspect, the invention includes a method of treating a condition associated with oxidative stress, aging or DNA damage in a subject, comprising administering to the subject a therapeutically effective amount of a pharmaceutical composition comprising a homolog selected from the group consisting of Pachytene Checkpoint 2 (PCH-2) and BMK-1.

In still another aspect, the invention includes a method of inducing cell death comprising administering a composition to inhibit a homolog selected from the group consisting of Pachytene Checkpoint 2 (pch-2) and BMK-1.

In yet another aspect, the invention includes a method of decreasing longevity of a cell comprising administering a composition to inhibit a homolog selected from the group consisting of Pachytene Checkpoint 2 (pch-2) and BMK-1.

In various embodiments of the above aspects or any other aspect of the invention delineated herein, the composition comprises a modulator of the homolog. In some embodiments, the modulator is an activator of the homolog, such as an activator of the homolog that increases gene expression of a heat shock protein. In another embodiment, the modulator decreases expression of a regulator that promotes cell apoptosis. In yet another embodiment, the composition comprises an inhibitor of the homolog. In some embodiments, the modulator is an inhibitor of the homolog, such as an inhibitor of the homolog that decreases gene expression of a gene encoding the homolog. Examples of an inhibitor of the homolog may be selected from the group consisting of an antisense RNA, antigomer RNA, miRNA, siRNA, shRNA, and a CRISPR system. In still another embodiment, the inhibitor of the homolog decreases gene expression of a heat shock protein.

In another embodiment, the composition increases resistance of the cell to at least one of oxidative stress, apoptosis, heat shock stress, DNA damage, protein damage and aging. In yet another embodiment, the composition comprises a nucleic acid encoding the homolog.

In another embodiment, the homolog is selected from the group consisting of Thyroid receptor-interacting protein 13 (TRIP13) and a kinesin, such as KIF11.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

Figure 1A:
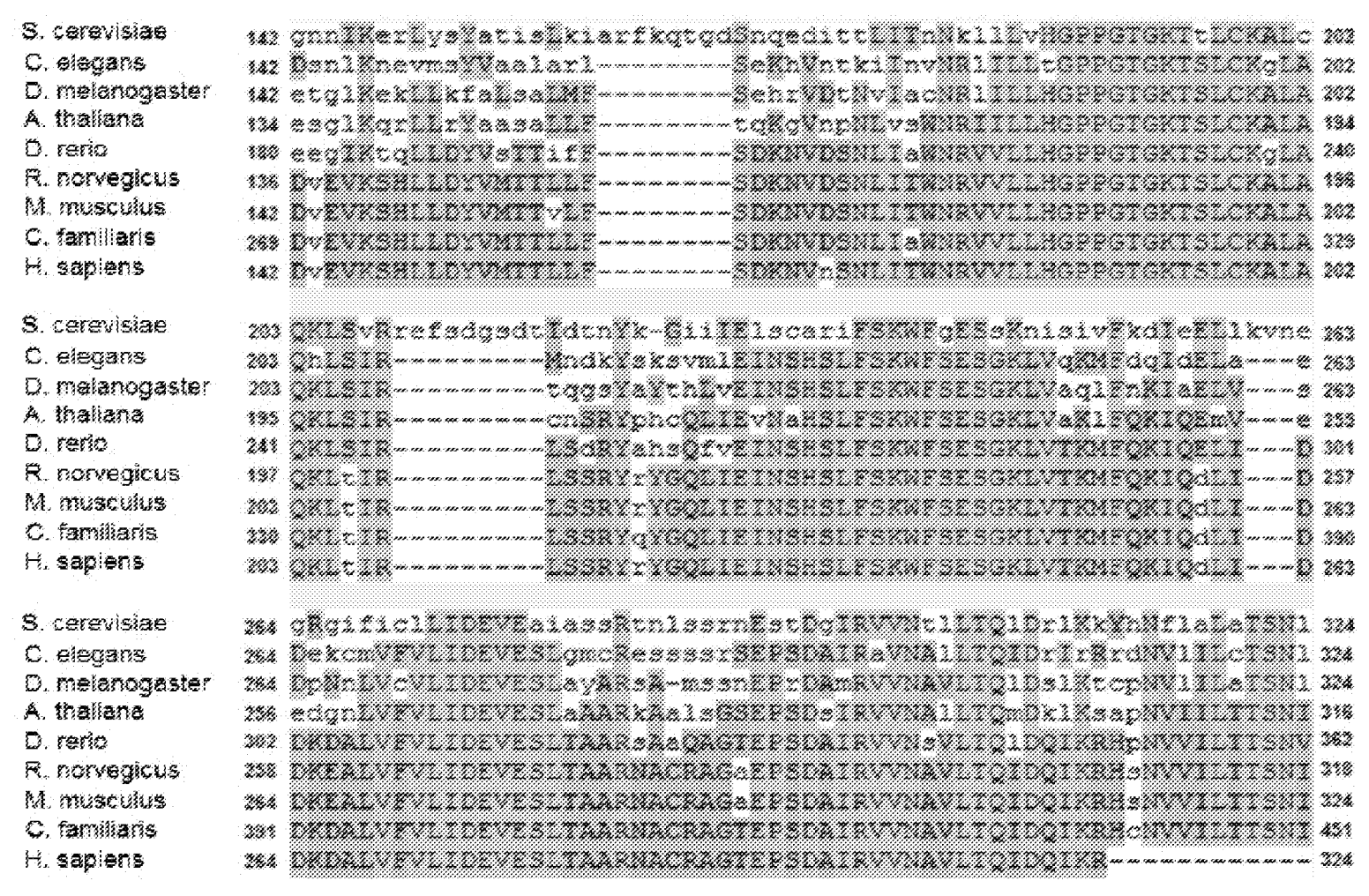

FIG. 1, comprising FIGS. 1A and 1B, shows pch-2 as an evolutionarily conserved gene whose expression declined with tissue aging across species. FIG. 1A shows the sequence alignment of pch-2 genes across species, yeast, worm, fly, rodent, and human are shown. FIG. 1B is a panel of graphs showing pch-2 and homologs of pch-2 mRNA expression changes with age in humans, mice and worms. * Indicates p<0.05.

FIG. 2, comprising FIG. 2A is a graph showing TRIP13 over-expression in fibroblast cells. After 600 μM $H_2O_2$ treatment, which causes oxidative stress, cell numbers were enhanced when compared to control cells, wild type (WT) and empty vector (p<0.0001). FIG. 2B is a graph showing TRIP13 over-expression in fibroblasts treated with 10 μM etoposide, which causes DNA strand breaks, for 3 days. Higher cell numbers were seen following treatment (p<0.001). FIG. 2C is a graph showing that the TRIP13 cells demonstrated significantly higher resistance to UV radiation, which causes DNA and protein damage, when compared to the control groups (p<0.01). (Relative cell survival was compared to numbers of cells plated, prior to culturing and stressors.) * Indicates significant differences between groups.

FIG. 3, comprising FIG. 3A is a blot showing genotyping experimental animals. The band for pch-2 appeared as a band at 1670 bp indicating the transgene was present in the pch-2 over-expressing line and not in wild type animals ("WT"). FIG. 3B is a graph showing qRT-PCR validation of pch-2 over-expression in worm lines by using transgene-specific primers to detect increased pch-2 gene expression (p<0.01). FIG. 3C is a graph showing lifespan measurements conducted in both WT (GFP-expressing, n=126) and pch-2 over-expressing (n=140) animals. Both median lifespan and maximum lifespans of pch-2 over-expressing lines showed a 25% extension when compared to WT lines (p<0.001, p values were derived from student t-test and log-rank test). FIG. 3D is a graph showing the median survival of pch-2 over-expressing lines (n=33), after 4 mM paraquat treatment, which causes oxidative stress, was increased by 40%, and the maximum survival of pch-2 over-expressing lines was increased 150% (n=30) (p<0.001). FIG. 3E is a graph showing that the median survival of pch-2 over-expressing lines (n=49) was increased 45% after UV radiation when compared to WT (n=45) (p<0.001). FIG. 3F is a graph showing the median survival of pch-2 over-expressing lines (n=62) with heat shock was increased by 85% when compared to WT (n=52) (p<0.001).

FIG. 4, comprising FIGS. 4A-4C, shows the inhibition of pch-2 and sir-2 expression by RNAi impacted lifespan in worms. FIG. 4A is a graph showing the shortened lifespan, both median (62%, 64%) and maximum (70%, 78%), was caused by pch-2 and sir-2 specific RNAi (n=81, 65), as compared to RNAi vector lines (n=63) (p<0.0001). FIG. 4B is a panel of graphs showing RNAi of pch-2 in WT worms resulted in significantly reduced expression of pch-2, ~70% validated by qRT-PCR, with no significant effect on sir-2 transcripts. FIG. 4C is a panel of graphs showing RNAi of sir-2 in WT worms, resulted a significant reduction of sir-2 expression, about 50% by qRT-PCR validation, without notable effect on pch-2 expression (*p<0.001).

FIG. 5, comprising FIG. 5A is a graph showing the shortened lifespan, both median (30%) and maximum (56%), was induced by pch-2-specific RNAi in C. elegans that was engineered to over-express pch-2 (n=101), as compared to RNAi vector lines (n=60) (p<0.0001). FIG. 5B is a graph showing qRT-PCR validated the RNAi effect, indicating a significant reduction (~70%) of pch-2 transcripts in pch-2 over-expressing worms treated with RNAi. ***p<0.001.

FIG. 6, comprising FIGS. 6A-6C, shows RNAi inhibition of both pch-2 in sir-2.1 over-expressing worms. Sir-2.1 in pch-2 over-expressing worms was found to shorten lifespan. FIG. 6A is a graph showing curves for the lifespans of sir-2.1 over-expressing worms (circles and large squares) and curves for lifespans of pch-2 over-expressing worms (small squares and triangles). In sir-2 over-expressing worms, pch-2 RNAi significantly decreased lifespan (56% and 75% decrease in median and maximum lifespan, respectively). In pch-2 over-expressing worms, sir-2.1 RNAi induced a 57% and 70% decrease in median and maximum lifespans (p<0.0001 for both effects). FIG. 6B is a panel of graphs showing that qRT-PCR validated the RNAi effect, indicating a significant reduction (~90%) of pch-2 transcripts in sir-2 over-expressing worms treated with pch-2 RNAi. FIG. 6C is a panel of graphs showing that qRT-PCR validated the significant reduction (~70) of sir-2 transcripts in pch-2 over-expressing worms treated with sir-2 RNAi. *p<0.001.

FIG. 7 is an illustration showing the proposed interactions of pch-2 and sir-2 in aging in C. elegans. Based on the data, pch-2 may, similar to sir-2, affect the aging process of C. elegans. Briefly, pch-2 may play a role in surveillance of DNA damage and chromatin regulation, in concert with sir-2. Reduction of pch-2 expression may induce genome instability and transcriptional dysregulation, and, therefore, may promote aging in C. elegans.

FIG. 8, comprising FIG. 8A is a graph showing mRNA quantification. FIG. 8B includes a blot and graph showing protein quantification.

FIG. 10, comprising FIGS. 10A and 10B, is a panel of images showing Bmk-1 is an evolutionarily conserved gene and its expression declines with tissue aging across species. FIG. 10A is an image showing sequence alignment of bmk-1 protein across species ranging from yeast to human. FIG. 10B is an image showing KIF11 mRNA expression changes with age in human and mouse. Y-axis represents the relative expression level of KIF11 was normalized to β-actin, and n>3 for each age group. * indicates p<0.05.

FIGS. 11A-11D, is a panel of graphs showing Bmk-1 over-expression extended lifespan and bmk-1 inhibition by RNAi shortened lifespan in C. elegans. FIG. 11A is a graph showing qRT-PCR validation of bmk-1 over-expression in worm lines using transgene-specific primers (* indicates p<0.01). Y-axis represents the relative expression level of bmk-1 normalized to act-1, and n≥10 for each group. FIG. 11B is a graph showing lifespan measurements for both WT (GFP-expressing, n=126) and bmk-1 over-expressing (n=161) animals. Both median lifespan and maximum lifespan of bmk-1 over-expressing lines demonstrated a 25% extension when compared to WT lines (p<0.001, p values were derived from student t-test and log-rank test). FIG. 11C is a graph showing qRT-PCR that validated the RNAi effect, indicating a significant reduction (~64%) of bmk-1 transcripts in WT worms treated with bmk-1 RNAi. Y-axis represents the relative expression level of bmk-1 normalized to act-1, and n≥10 for each group. * indicates p<0.01. FIG. 11D is a graph showing the shortened lifespan, both median (32%) and maximum (15%), was induced by bmk-1-specific RNAi in *C. elegans* (n=82), as compared to RNAi vector lines (n=75) (p<0.0001).

FIGS. 12A-12C, is a panel of graphs showing Bmk-1 over-expression enhanced the stress response in *C. elegans*. FIG. 12A is a graph showing the median survival of bmk-1 over-expressing lines (n=37) was unchanged as compared to WT (GFP-expressing) lines after 4 mM paraquat treatment, which causes oxidative stress, but the maximum survival of bmk-1 over-expressing lines was increased 115% (n=30) (p<0.001). FIG. 12B is a graph showing the median survival of bmk-1 over-expressing lines (n=54) was increased 15% after UV radiation, which causes DNA and protein damage, when compared to WT (n=49) (p<0.01). FIG. 12C is a graph showing the median and maximum survivals of bmk-1 over-expressing lines (n=42) after heat shock treatment, which causes heat stress, were increased by 110% and 43%, respectively, when compared to WT (n=45) (p<0.001).

FIGS. 13A-13D, is a panel of graphs showing Hsp-16 expression was elevated after heat shock in bmk-1 over-expressing *C. elegans*. FIG. 13A is a graph showing that expression of hsp-12 was not changed significantly between WT and bmk-1 over-expressing lines. FIG. 13B is a graph showing that expression of hsp-16 was increased significantly in bmk-1 over-expressing lines when compared to WT control lines (p<0.05). FIG. 13C is a graph showing that expression of hsp-70 was not significantly different between WT and bmk-1 over-expressing lines. FIG. 13D is a graph showing expression of ced-3 decreased significantly in bmk-1 over-expressing lines when compared to WT control lines (* indicates p<0.05). Y-axis represents the relative expression levels of hsp12, hsp16, hsp70, and ced-3 normalized to act-1, respectively; n≥10 for each group.

FIGS. 14A-14D, is a panel of graphs showing that RNAi inhibition of hsp-16 in bmk-1 over-expressing worms shortened lifespan and weakened heat shock response. FIG. 14A is a graph showing hsp-16 RNAi in bmk-1 over-expressing worms resulted in significantly reduced expression, over 80% as validated by qRT-PCR. Y axis represents the relative expression level of hsp-16 as it was normalized to act-1, and n≥10 for each group (*p<0.001). FIG. 14B is a graph showing bmk-1 RNAi in hsp-16 over-expressing worms resulted in significantly reduced expression, over 70% as validated by qRT-PCR. Y axis represents the relative expression level of bmk-1 as it was normalized to act-1, and n≥10 for each group (*p<0.001). FIG. 14C is a graph showing lifespans of bmk-1 over-expressing worms and hsp-16 over-expressing worms. In bmk-1 over-expressing worms, hsp-16 RNAi significantly decreased lifespan (77% and 78% decrease in median and maximum lifespan, respectively) (p<0.0001 for both). However, in hsp-16 over-expressing worms, bmk-1 RNAi did not change either median or maximum lifespans. FIG. 14D is a graph showing hsp-16 RNAi significantly deteriorated bmk-1 over-expressing worms' response to heat shock with a shortening of about ⅓ maximum lifespan (p<0.0001, p values were derived from student t-test and log-rank test. n=28 for RNAi vector group and n=37 for hsp-16 RNAi group).

DETAILED DESCRIPTION

Definitions

Figure 1B:
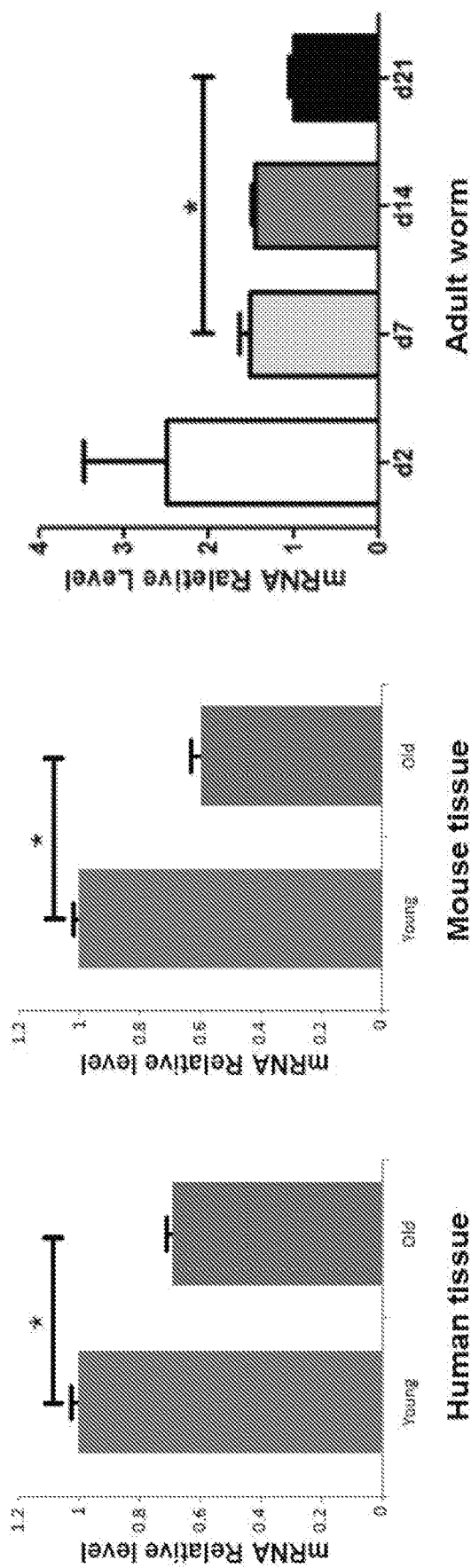

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a cell that has been sufficiently stimulated to induce a measurable activity, such as detectable cellular proliferation. Activation can also be associated with induced gene expression, and detectable effector functions. The term "activated cells" refers to, among other things, cells that are performing the measurable activity.

The term "aging" as used herein refers to the result of progressive decline in the proliferative capacity and/or lifespan of a cell. Each cell is programmed for a certain number of cell divisions and at the end of that time, proliferation may halt and/or the cell may enter apoptosis.

The term "agonist" is meant to include an agent, molecule or compound that activates or promotes a biological response. The agonist often mimics the action of a naturally occurring molecule.

The term "antagomir" is meant to include a class of oligonucleotides that prevent other molecules from binding to a site on a mRNA molecule, thus preventing translation of the mRNA. The antagomir may be a small synthetic RNA, such as a chemically engineered oligonucleotide, that is complementary to the specific miRNA. The antagomirs have some sort of modification, such as 2'-methoxy groups or phosphorothioates, to reduce degradation.

The term "antagonist" is meant to include an agent, molecule, or compound that inhibits a biological response.

The antagonist can prevent or decrease ligand-or agonist-mediated responses. The antagonist may disrupt interaction of receptors and ligands, thereby inhibiting activation. Other antagonists may have affinity for other agonists and compete to bind the cognate binding partner, thereby preventing or reducing the ability of a cognate ligand or agonist to induce activation.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

As used herein, the term "autologous" is meant to refer to any material derived from the same individual to which it is later to be re-introduced into the individual.

"Allogeneic" refers to a graft derived from a different animal of the same species.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

The term "CRISPR/CAS," "clustered regularly interspaced short palindromic repeats system," or "CRISPR" refers to DNA loci containing short repetitions of base sequences. Each repetition is followed by short segments of spacer DNA from previous exposures to a virus. Bacteria and archaea have evolved adaptive immune defenses termed CRISPR-CRISPR-associated (Cas) systems that use short RNA to direct degradation of foreign nucleic acids. In bacteria, the CRISPR system provides acquired immunity against invading foreign DNA via RNA-guided DNA cleavage.

In the type II CRISPR/Cas system, short segments of foreign DNA, termed "spacers" are integrated within the CRISPR genomic loci and transcribed and processed into short CRISPR RNA (crRNA). These crRNAs anneal to trans-activating crRNAs (tracrRNAs) and direct sequerice-specific cleavage and silencing of pathogenic DNA by Cas proteins. Recent work has shown that target recognition by the Cas9 protein requires a "seed" sequence within the crRNA and a conserved dinucleotide-containing protospacer adjacent motif (PAM) sequence upstream of the crRNI-binding region.

To direct Cas9 to cleave sequences of interest, crRNA-tracrItNA fusion transcripts, hereafter referred to as "guide RNAs" or "gRNAs" may be designed, from human U6 polymerase III promoter. CRISPR/CAS mediated genome editing and regulation, highlighted its transformative potential for basic science, cellular engineering and therapeutics.

The term "CRISPRi" refers to a CRISPR system for sequence specific gene repression or inhibition of gene expression, such as at the transcriptional level.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

By "fragment" is meant a portion of a polynucleotide or nucleic acid molecule. This portion contains, preferably, at least 10%, 20%, 30%, 40%, 50%, 60%, 70%, 80%, or 90% of the entire length of the reference nucleic acids. A fragment may contain 10, 20, 30, 40, 50, 60, 70, 80, 90, or 100, 200, 300, 400, 500, 600, 700, 800, 900, 1000, 1500, 2000 or 2500 (and any integer value in between) nucleotides. The fragment, as applied to a nucleic acid molecule, refers to a subsequence of a larger nucleic acid. A "fragment" of a nucleic acid molecule may be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

The term "homolog" as used herein, refers to a shared ancestry between a pair of structures, genes, or proteins in different species. In one example,. Pachytene CHeckpoint 2 or pch-2 or PCH-2 is found in C. elegans and the human homolog of the pch-2 or PCH-2 includes Thyroid receptor-interacting protein 13 (TRIP13) or TRIP13. In another example, silent information regulator 2 (SIR2) gene in S. cerevisiae and the human homolog of the SIR2 includes Sirtuin 1 or SIRT1. In another example, bmk-1 or BMK-1 is found in C. elegans and the mouse or human homolog of bmk-1 includes a gene or protein from the kinesin-1 through kinesin-14 superfamilies, such as Kinesin-11 or KIF11.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two molecules particularly between two amino acid molecules, such as, between two polypeptide molecules or two polynucleotide molecules, such as between two DNA sequences. When two amino acid sequences have the same residues at the same positions; e.g., if a position in each of two polypeptide molecules is occupied by an Arginine, then they are identical at that position. When two nucleotide sequences have the same nucleotides at the same positions; e.g., if a position in each of two poly nucleotide molecules is occupied by a guanosine, then they are identical at that position. The identity or extent to which two sequences have the same molecule at the same positions in an alignment is often expressed as a percentage. The identity between two sequences is a direct function of the number of matching or identical positions; e.g., if half (e.g., five positions of ten positions in length) of the positions in two sequences are identical, the two sequences are 50% identical; if 90% of the positions (e.g., 9 of 10), are matched or identical, the two sequences are 90% identical.

As used herein, the term "inhibit" is meant to refer to a decrease in biological state. For example, the term "inhibit" may be construed to refer to the ability to negatively regulate the expression, stability or activity of a protein, including but not limited to transcription of a protein mRNA, stability of a protein mRNA, translation of a protein mRNA, stability of a protein polypeptide, a protein post-translational modifications, a protein activity, a protein signaling pathway or any combination thereof.

By "inhibitor" is meant a molecule that decreases or prevents a biological activity, such as gene expression. The inhibitor can disrupt gene expression, either directly or indirectly, and/or prevent effective transcription or translation of the gene to decrease or prevent its expression. Inhibitors may also include, but are not limited to, small molecule inhibitors, antagonists, neutralizing antibodies, and inhibitory oligonucleotides.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "life span" is meant the length of time an organism exists or is expected to exist.

The term "health span" refers to the length of time an organism exists in a healthy or free from disease state.

By "microRNA" or "miRNA" or "miR" is meant a small non-coding RNA, which functions in transcriptional and/or post-transcriptional regulation of gene expression.

By the term "modified" as used herein, is meant a changed state or structure of a molecule or cell of the invention. Molecules may be modified in many ways, including chemically, structurally, and functionally. Cells may be modified through the introduction of nucleic acids.

The term "modulator" as used herein, refers to a treatment with an agent, molecule, or compound that acts to increase or decrease a level of a response of a gene or protein in a cell or subject compared with the level of a response in the absence of the treatment with the agent, molecule, or compound. The modulator may include, but is not limited to, any agent, molecule or compound that alters gene expression, alters an upstream activator or inhibitor gene or gene product, such as a transcription factor, alters gene product activity, alters a cis-acting or trans-acting factor, or acts by any other mechanism to alter the gene or gene product.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting native expression, translation or response thereby mediating a beneficial therapeutic response in a subject, preferably, a human. Modulating may include, but is not limited to, a change in gene expression, a change in an upstream activator or inhibitor gene or gene product, such as a transcription factor, a change in gene product activity, a change in a cis-acting or trans-acting factor, or an act by any other mechanism that results in alteration of the gene or gene product.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "over-expressed" or "over-expression" is intended to indicate an abnormal level of expression in a cell. Over-expression may be in the form of a disease like a tumor relative to the level of expression in a normal cell from that tissue or organ.

The term "oxidative stress" refers to an imbalance between the systemic manifestation of reactive oxygen species and a biological system's ability to readily detoxify the reactive intermediates or to repair damage caused by the reactive species. Toxic effects include the production of perioxides and free radicals that may damage components of a cell, including proteins, lipids, and DNA.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™ and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By "reference" is meant a standard or control. A "reference " is a defined standard or control used as a basis for comparison.

As used herein, "sample" or "biological sample" refers to anything, which may contain the cells of interest (e.g., cancer or tumor cells thereof) for which the screening method or treatment is desired. The sample may be a biological sample, such as a biological fluid or a biological tissue. In one embodiment, a biological sample is a tissue sample including pulmonary arterial endothelial cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

By "shRNA" is meant sequences of RNA that make a tight hairpin that can be used to silence target gene expression via RNA interference (RNAi). Expression of the shRNA in cells can be obtained by delivery of plasmids or viral or bacterial vectors.

By "siRNA" is meant double stranded RNA molecules, usually around 20-30 nucleotides in length, that are capable of interfering in gene expression. The siRNA molecules may have regions that are complementary to specific genes that decrease translation of these genes.

The term "small molecule" refers to a peptide having about 10, 11, 12, 13, 14, 15, 16, 17, 18, 19, or 20 amino acids with the capacity to bind a target, such as a molecule, or antigen. The small molecule comprises a low molar mass, such as less than about 12 kD, 11 kD, 10 kD, 9 kD, 8 kD, 7 kD, 6 kD, 5 kD, or any molar mass therebetween or less. In some embodiments, the small molecule is a small molecule extracellular domain of an affinity molecule chimeric receptor. In some embodiments, the small molecule is a small molecule binding domain of a bispecific affinity molecule. Small molecule may be characterized by their ability to bind a target and their structure. In some embodiments, the small molecule comprises at least one helix, such an alpha-helix, or two helices, three helices or more. The small molecule may also be chemically inert and withstand high temperatures, such as 85° C. or higher.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes methods and compositions to increase longevity of a cell or organism and increase cellular resistance to stress. Methods of inducing or inhibiting gene expression or gene products associated with longevity or stress resistance are also described.

Pachytene Checkpoint 2 (PCH-2)

The Pachytene Checkpoint 2 (pch-2) gene has been studied for its functions in monitoring and correcting DNA errors during cell mitosis. Pachytene Checkpoint 2 or pch-2 plays a role in chromosome recombination during meiosis. In budding yeast, PCH2 and silent information regulator 2 (SIR2) are found predominantly in the nucleolus. Mutation of PCH2, or SIR2, bypasses checkpoint-induced pachytene arrest, and PCH2 and SIR2 are both needed to prevent meiotic interhomolog recombination within the repeated ribosomal RNA genes that are present in the nucleolus.

Increased expression of the SIR2 family proteins, now called the "sirtuins," has been shown to enhance lifespan in a range of organisms, including *S. cerevisiae, C. elegans, D. melanogaster,* and *M. musculus*. Brain-specific Sirt1-over-expressing (BRASTO) transgenic mice demonstrated a significant life span extension of 11%, and aged BRASTO mice also exhibited a clear delay in aging phenotypes. Overexpression of Sirt6, another mammalian homolog of Sirt2, extends lifespan in male mice around 15%, but had no effect in females. However, no functional association between PCH2 and SIR2 has been linked to aging or to lifespan.

Exemplary pch-2 sequences include the human homolog, Thyroid receptor-interacting protein 13 (TRIP13), sequence found at GenBank Accession No. NM_001166260 or NP_001159732, or a fragment thereof, and the mouse homolog, Trip13, sequence found at NM_027182 or NP_081458, or a fragment thereof.

BMK-1

BMK-1 is a member of the kinesin-1 family, a large super family of motor proteins that participate in various critical biological processes, including mitosis and intracellular transport of vesicles and organelles. Kinesins comprise a long coiled-coil stalk with a cargo binding tail at one end, and a globular tail domain at the other end. The highly conserved motor domain contains both microtubule and nucleotide binding sites. Kinesin proteins are localized to centrosomes, spindle microtubules, and the spindle midzone, and act during the early stages of mitosis to facilitate centrosome separation and bipolar spindle assembly. These processes are essential for accurate chromosome segregation and progress through the cell cycle.

In *C. elegans*, BMK-1 has been reported to serve a novel function as a "brake" that slows down the rate of anaphase spindle-pole separation. The BMK-1 homolog in *Drosophila* contributes to a range of functions in mitosis, all of which are consistent with it exerting outward forces on spindle poles by sliding microtubules relative to a static spindle matrix, or by crosslinking and sliding apart adjacent pairs of antiparallel interpolar microtubules.

Exemplary homologs of bmk-1 and BMK-1 include members of the mouse and human kinesin superfamilies, kinesin-1 through kinesin-14. For example, KIF11, the mouse and human equivalent of the *C. elegans*, BMK-1, is a member of the 14 kinesin subfamilies, which are classified by the phylogenetic analysis for the motor domain. KIF11 normally functions as a mitotic cell cycle and checkpoint regulator. Premature separation of centrosomes decreases the requirement for KIF11 in spindle assembly, accelerates mitosis, and decreases the rate of chromosome mis-segregation. Neither BMK-1 nor KIF11 has been linked to aging or to lifespan in either mammals or lower organisms. The modulated expression of bmk-1 in *C. elegans* is described herein to play an important role in lifespan determination.

Compositions

In one aspect, the invention includes a composition comprising a nucleic acid encoding a homolog selected from the group consisting of Pachytene Checkpoint 2(PCH-2) and BMK-1. In another aspect, the invention includes a composition comprising a modulator of a homolog selected from the group consisting of Pachytene Checkpoint 2 (PCH-2) and BMK-1. In one embodiment, the homolog is selected from the group consisting of Thyroid receptor-interacting protein 13 (TRW13) and a kinesin, such as Kinesin-11 (KIF11). In another embodiment, the homolog is a protein. In some embodiments, the composition may include the protein homologs of PCH-2 and BMK-1, such as TRIP13 and KIF11.

In one embodiment, the modulator is an activator of the homolog. In such embodiments, the composition increases resistance of a cell to at least one of oxidative stress, apoptosis, DNA damage, aging and protein damage. The modulator of the homolog may include any agent, molecule or compound that increases gene expression of the homolog; activates an upstream activator or inhibitor of a pch-2 or bmk-1 gene or a pch-2 or bmk-1 homologous gene, such as a transcription factor; increases protein activity of PCH-2 or BMK-1 or a PCH-2 or BMK-1 homolog; inhibits a cis-acting or trans-acting factor, or acts by any other mechanism that activate a pch-2 or bmk-1 gene or a pch-2 or bmk-1 homologous gene. In one embodiment, the activator of the homolog increases gene expression of a heat shock protein, such as HSP-16. In another embodiment, the modulator decreases expression of a regulator that promotes cell apoptosis, such as CED-3. In some embodiments, the composition may include any agent, molecule or compound that increases gene expression or protein stability of the homologs of PCH-2 and BMK-1, such as an agent that affects RNA expression or stability, miRNAs, small molecules that affect gene expression, RNAi, and a CRISPR system.

In another embodiment, the modulator is an inhibitor of the homolog. In one exemplary embodiment, the inhibitor of the homolog decreases gene expression of a gene encoding the homolog. In such embodiments, the gene expression inhibitor may be an antisense RNA, antigomer RNA, miRNA, siRNA, shRNA, and a CRISPR system. In one embodiment, the composition induces cell death or apoptosis. In another embodiment, the composition decreases longevity of a cell. The modulator of homolog may include any agent, molecule or compound that decreases gene expression of the homolog; inhibits an upstream activator or inhibitor of a pch-2 or bmk-1 gene or a pch-2 or bmk-1 homologous gene, such as a transcription factor; decrease protein activity of PCH-2 or BMK-1 or a PCH-2 or BMK-1 homolog; inhibits a cis-acting or trans-acting factor, or acts by any other mechanism to inhibit a pch-2 or bmk-1 gene or a pch-2 or bmk-1 homologous gene. In one embodiment, the inhibitor of the homolog decreases gene expression of a heat shock protein, such as HSP-16. In some embodiments, the composition may include any agent, molecule or compound that decreases gene expression or protein stability of the homologs of PCH-2 and BMK-1, such as an agent that affects RNA expression or stability, antisense RNAs, antigomer RNAs, siRNAs, shRNAs, miRNAs, small molecules that affect gene expression, RNAi, and a CRISPR system.

In some embodiments, a method is described for treating a condition associated with oxidative stress, aging or DNA damage in a subject by administering a therapeutically effective amount of a pharmaceutical composition comprising a modulator of a homolog selected from the group consisting of Pachytene Checkpoint 2(PCH-2) and BMK-1. The present invention also includes methods to increase cellular resistance to stress and to cellular aging and organismal aging, increase longevity of a cell, and treat oxidative stress. Alternatively, the present invention includes methods to induce cellular death or apoptosis or decrease longevity of a cell.

Nucleic Acids

The present invention includes a composition comprising a nucleic acid encoding a homolog of Pachytene Checkpoint 2 (PCH-2) or BMK-1, when introduced into a cell can increase expression of the homolog. Methods of introducing nucleic acids into a cell include physical, biological and chemical methods. Physical methods for introducing a polynucleotide, such as DNA like cDNA, into a host cell include calcium phosphate precipitation, lipofection, particle bombardment, microinjection, electroporation, and the like. DNA, like cDNA, can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendorf, Hamburg Germany). DNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001)).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Therapy

The composition described herein may be included in a composition for therapy in a subject in need thereof. In one aspect, the composition induces a homolog of Pachytene Checkpoint 2 (PCH-2) or BMK-1 for increasing longevity of a cell or an organism as described herein. In another aspect, the composition induces a homolog of Pachytene Checkpoint 2 (PCH-2) or BMK-1 for increasing cellular resistance to stress, oxidative stress, aging or DNA damage, as described herein. The composition may include a pharmaceutical composition and further include a pharmaceutically acceptable carrier. A therapeutically effective amount of the pharmaceutical composition may be administered.

In one aspect, the invention includes a method for increasing longevity of a cell or an organism comprising administering a composition to induce a homolog of Pachytene Checkpoint 2 (PCH-2) or BMK-1. In another aspect, the invention includes a method for increasing cellular resistance to stress, aging or DNA damage in a cell comprising contacting the cell with a composition to induce a homolog of Pachytene Checkpoint 2 (PCH-2) or BMK-1. In some embodiments, the composition comprises a nucleic acid encoding the homolog of PCH-2 or BMK-1. In another embodiment, the composition comprises a modulator of the pch-2 homolog or BMK-1 homolog. The modulator is an activator of the PCH-2 homolog or BMK-1 homolog.

In another aspect, the invention includes a method of inducing cell death or apoptosis comprising administering a composition to inhibit a homolog of Pachytene Checkpoint 2 (PCH-2) or BMK-1. In yet another aspect, the invention includes a method of decreasing longevity of a cell comprising administering a composition to inhibit a homolog of Pachytene Checkpoint 2 (PCH-2) or BMK-1. In some embodiments, the composition comprises an inhibitor of the PCH-2 homolog or BMK-1 homolog. In some embodiments, the inhibitor of the PCH-2 homolog decreases gene expression of a pch-2 gene. In some embodiments, the inhibitor of the BMK-1 homolog decreases gene expression of a bmk-1 gene. In such embodiments, the inhibitor is selected from the group consisting of an antisense RNA, antigomer RNA, miRNA, siRNA, shRNA, and a CRISPR system.

In another aspect, the invention includes a method of treating a condition associated with oxidative stress, aging or DNA damage in a subject, comprising administering to the subject a therapeutically effective amount of a pharmaceutical composition comprising a nucleic acid encoding a homolog of Pachytene Checkpoint 2(PCH-2) or BMK-1 or a pharmaceutical composition comprising a modulator of a homolog of Pachytene Checkpoint 2 (PCH-2) or BMK-1. The composition can be administered to an animal, preferably a mammal, even more preferably a human, to suppress oxidative stress, such as those common to a cancer, tumors, a proliferative disease, a precancerous condition, and a non-cancer indication, including brain cancer (e.g., a glioma), bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof, and the like. In addition, the composition of the present invention can be used for the treatment of any condition in which a diminished or otherwise inhibited immune response is desirable to treat or alleviate the disease. In one aspect, the invention includes treating a condition associated with oxidative stress, aging or DNA damage in a subject, comprising administering to the subject a therapeutically effective amount of a pharmaceutical composition.

The composition generated as described herein can also be used to treat inflammatory disorders. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

In another embodiment, the invention includes the composition described herein for use in a method of treating oxidative stress, aging, or DNA damage in a cell in need thereof. In another embodiment, the invention includes the composition described herein for use in a method of treating oxidative stress in a subject in need thereof. In yet another aspect, the composition described herein is for use in the manufacture of a medicament for the treatment of a condition or disease in a subject in need thereof.

The composition of the invention can be administered in dosages and routes and at times to be determined in appropriate pre-clinical and clinical experimentation and trials. The compositions may be administered multiple times at dosages within these ranges. Administration of the composition of the invention may be combined with other methods useful to treat the desired disease or condition as determined by those of skill in the art.

The composition of the invention may be administered to autologous, allogeneic or xenogeneic cells and then those cells may be administered to a subject undergoing therapy.

The administration of the composition of the invention may be carried out in any convenient manner known to those of skill in the art. The composition of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i. v.) injection, or intraperitoneally. In other instances, the composition of the invention are injected directly into a site of inflammation in the subject, a local disease site in the subject, a lymph node, an organ, a tumor, and the like.

The composition described herein can also be administered using any number of matrices. The present invention utilizes such matrices within the novel context of acting as an artificial lymphoid organ to support, maintain, or modulate the immune system, typically through modulation of immune cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

Pharmaceutical Compositions

Pharmaceutical compositions of the present invention may comprise an activator or an inhibitor of a homolog of Pachytene Checkpoint 2 (PCH-2) or BMK-1 as described herein, in combination with one or more pharmaceutically or physiologically acceptable carriers, diluents or excipients. In one aspect, the invention includes a pharmaceutical composition comprising a nucleic acid encoding a homolog of Pachytene Checkpoint 2 (PCH-2) or BMK-1. In another aspect, the invention includes a pharmaceutical composition comprising a modulator of a homolog of Pachytene Checkpoint 2 (PCH-2) or BMK-1. In yet another aspect, the invention includes a pharmaceutical composition comprising any of the compositions described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an effective amount", or "therapeutic amount" is indicated, the precise amount of the compositions of the present invention to be administered can be determined by a physician with consideration of individual differences in age, weight, immune response, and condition of the patient (subject). It can generally be stated that a pharmaceutical composition comprising the modified T cells described herein may be administered at a dosage of $10^4$ to $10^9$ cells/kg body weight, preferably $10^5$ to $10^6$ cells/kg body weight, including all integer values within those ranges. Compositions may also be administered multiple times at these dosages. The composition can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer the composition to a subject and then subsequently redraw blood (or have an apheresis performed), induce gene expression in cells therefrom according to the present invention, and reinfuse the patient with these gene expressing cells. This process can be carried out multiple times every few weeks. In certain embodiments, gene expression can be activated from blood draws of from 10 ml to 400 ml. In certain embodiments, gene expression are activated from blood draws of 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of cells.

In certain embodiments of the present invention, cells, induced to express the genes by methods described herein, or other methods known in the art, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993).

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Components or downstream targets of many signaling pathways, such as insulin/IGF-1 and TOR, in concert with genes involved in cellular metabolism and bioenergetics can extend worm lifespans 20% or more. The C. elegans gene, pch-2, and homologs, including TRIP13 in humans, have been studied for their functions in cell mitosis and meiosis, but have never been implicated in lifespan regulation. Over-expression of TRIP13 in human fibroblasts is shown herein to confer resistance to environmental stressors, such as UV radiation and oxidative stress. Furthermore, pch-2 over-expression in C. elegans extended worm lifespans, and enhanced worm survival in response to various stressors. Conversely, reducing pch-2 expression with RNAi shortened worm lifespans. Additional genetic epistasis analysis indicated that the molecular mechanism of pch-2 in worm longevity was similar to the functions of the sirtuin family, suggesting that pch-2 is another chromatin regulator for worm longevity. These findings suggest a novel function of the pch-2 gene involved in lifespan determination.

The bmk-1 gene also has important functions in chromosome segregation in C. elegans, as well as its mammalian homolog, KIF11. However, this gene has never been implicated in aging or lifespan regulation. The bmk-1 gene is shown herein to be an important lifespan regulator in worms. Reducing bmk-1 expression using RNAi shortened worm lifespans by 32%, while over-expression of bmk-1 extended worm lifespan by 25%, and enhanced heat-shock stress resistance. Moreover, bmk-1 over-expression increased the level of hsp-16 and decreased ced-3 in C. elegans. Genetic epistasis analysis revealed that hsp-16 was essential for lifespan extension by bmk-1. These findings suggest that BMK-1 may act through enhanced hsp-16 function to protect cells from stress and inhibit the apoptosis pathway, thereby conferring worm longevity.

The Materials and Methods used in the performance of the experiments disclosed herein are now described.

Nematode strains and maintenance. The C. elegans nematode strain N2 was used for all the experiments and was a gift from the Reinke lab. The sir-2 over-expressing line, LG394, was purchased from Caenorhabditis Genetics Center (CGC). All the C. elegans stocks, including constructed strains, were maintained at 25° C. on nematode growth medium agar (NGM) plates seeded with E. coli strain, OP50, as described in WormBook.

Molecular cloning. Multiple DNA fragments were cloned by using Gateway three-fragment vector construction kits. (Invitrogen, Carlsbad, Calif.).

Step 1: Three fragments were produced with flanking sites by PCR. Three fragments included a promoter (myo-3), a gift from Koelle lab; gene (GFP or pch-2); and 3'-UTR were amplified by PCR using primers that incorporated flanking attB4 and attB1r sites in the myo-3 fragment, flanking attB1 and attB2 sites in the GFP, pch-2 fragment, or bmk-1 genes, and flanking attB2r and attB3 sites in the 3'-UTR fragment. Templates for amplifying Myo-3, GFP, and 3'-UTR are others' plasmids (gift from Reinke lab), and the gene bmk-1 was amplified from C. elegans genomic DNA (gift from Reinke lab).

Step 2: Entry clones were generated by BP reactions. Three PCR products from step 1 and three donor vectors, P4-P1r, P1-P2, P2-P3, were used in three separate BP recombination reactions between an attB-flanked DNA fragment and an attP-containing donor vector to generate the entry clone. Three entry clones were generated: pENTR™L4-R1-myo-3, pENTR™L1-L2-GFP, pENTR™L1-L2-pch-2, pENTR™L1-L2-bmk-1, and pENTR™R2-L3-3'-UTR.

Step 3: Expression clones were generated by LR reactions. Expression clones were generated by LR reactions between an attL-containing entry clone and an attR-containing destination vector. Three entry clones from step 2 and the destination vector pDESTR™ R4 -R3 were used together in a single LR reaction to generate the expression clones pCFJ150 with the fragments, which were named pCFJ150-GFP, pCFJ150-pch-2, and pCFJ150-bmk-1.

Microinjection. A DNA mixture of 10 ng plasmid, pCFJ150-GFP, and 10 ng plasmid, pCFJ150-pch-2, and 50 ng carrier plasmid, pUC-19, was microinjected into the syncytial gonad of wild type N2 animals. A DNA mixture of 10 ng plasmid pCFJ150-GFP, and 10 ng plasmid pCFJ150-bmk-1, and 50 ng carrier plasmid pUC-19 was microinjected into the syncytial gonad of wild type N2 animals. After 48-72 hr, the progeny of injected worms were scored using a fluorescent stereomicroscope (Olympus S2×16). Each green transformed progeny was transferred to a separate NGM plate as an independent line using a worm pick. Only the lines for which the F1 progeny could pass the transgene onto their progeny with efficiencies (green positive worms as a fraction of all progeny) greater than 50% were kept and used in further experiments. GFP alone with the carrier DNA was injected to obtain control lines. Each transgenic line was maintained by transferring 5-10 green worms to a new NGM plate every 3-4 days.

Genotyping. Single adult worms were picked and put into 10 µl lysis buffer (50 mM KCl, 10 mM Tris pH8.3, 2.5 mM MgCl2, 0.45% NP40, 0.45% Tween 20, 0.01% gelatin) with fresh 1.0 mg/ml Proteinase K. Worms were digested at 60°

C. for an hour and 95° C. for 15 min. Digested lysate template was amplified by PCR using oligonucleotide primer sequences

```
Forward:
                                        SEQ ID NO: 1
5'-ctatgaccatgattacgccaagc, Reverse:
                                        SEQ ID NO: 2
5'-gatgatgaggattcacgacaca,
```

The PCR product was indicated by a 1670 bp band on a 1% agarose gel. The pch-2 and bmk-1 over-expressing lines were genotyped to ensure the over-expressors actually over-expressed pch-2 or bmk-1, respectively.

Lifespan assay. To quantify lifespan, L4 larvae from the age-synchronized population of worms were transferred to NGM plates supplied with 100 μg/ml Ampicillin and 500 nM 5-fluoro-20-deoxyuridine (FUDR) was seeded with sufficient OP50 bacteria. Worms were monitored by tapping their heads with a platinum worm pick every 1 or 2 days until they were dead. Worms were scored as dead if they did not respond by moving the head after tapping. Worms which had fled or crawled off the agar and died on the sides were censored and removed from analysis. At least three individual experiments were performed in each group.

Paraquat treatment and heat shock. Age-synchronized L4 larvae were first transferred to FUDR plates. After 24 hr, for the paraquat assay, young adults were moved to FUDR plates supplied with 4 mM paraquat for the duration of the experiment. For heat shock, the plates with young adult worms were moved to a 35° C. incubator for 2 hr, and then placed back in 25° C. conditions. All of the worms were subsequently monitored each day for survival, and survival curves were based on daily counting.

UV radiation. Young adult worms were irradiated on NGM plates without OP50 under a germicidal bulb (254 nm) at 0.1 J/cm2 by using an UV crosslinkers. (CL-1000 Ultraviolet Crosslinkers, LLC Upland, Calif., US). Then the worms were transferred to FUDR plates that were seeded with OP50. Worms were checked daily through their lives to generate survival curves.

RNAi induction. Gene knock down by RNAi was performed by feeding the worms with bacteria which produced dsRNA against the gene of interest. RNAi for pch-2 and bmk-1 were gifts (Weidhaas lab). Briefly, on the first day, the RNAi clone in *E. coli* was incubated overnight at room temperature on RNAi agar plates with 25 μg/ml carbenicillin and 1 mM isopropylthiogalactosidase (IPTG) to induce dsRNA expression. On the second day, L4 larvae were transferred to the seeded plates to be monitored for their life spans. Bacteria containing RNAi empty vector were used as food for the control group. The sir-2 over-expressing line, LG394, and WT worms were studied with RNAi.

RNA isolation and Quantitative PCR. Total RNA was isolated from 10 adult worms per sample using RNeasy mini kit (QIAGEN Valencia, Calif.). Nematodes were washed in M9 buffer three times and excess M9 was carefully removed. The samples were re-suspended in 350 μL lysis buffer with β-mercaptoethanol, mixed with an equal volume of 70% ethanol. The mixture was transferred to a spin column and followed by washing according the manufacturer's protocol. DNase digestion was performed in the column and RNA was eluted in 13 μL RNase-free water. Total of 12 μL RNA was used to synthesize cDNA using the Ominscript kit (QIAGEN, Valencia, Calif.). For real-time PCR, each 25 μL reaction containing 12.5 μL of 2× Sybr-Green supermix (Bio-Rad, Waltham, Mass.), 0.4 μM of each primer, and 2 μL of template cDNA was performed on a C1600 Thermal Cycler (Bio-Rad, Waltham, Mass.). Relative gene expression level was normalized to act-1 and calculated using the ΔΔCt (cycle threshold) method.

TABLE 1

Cloning primers.

| | |
|---|---|
| attB1-bmk-1-F | 5'-ggggacaagtttgtacaaaaaagcaggctcgttggattcgacaatggcatcc, SEQ ID NO: 3 |
| attB2-bmk-1-R | 5'-ggggaccactttgtacaagaaagctgggtctgtgcgttagttttcgaaatc, SEQ ID NO: 4 |
| attB4-Pmyo3-F | 5'-ggggacaactttgtatagaaaagttgaacggctataataagttctt, SEQ ID NO: 5 |
| attB1r-Pmyo3-R | 5'-ggggactgcttttttgtacaaacttgttctagatggatctagtgg, SEQ ID NO: 6 |
| bmk-1-R | 5'-tcaacttgaatgtggttctcc, SEQ ID NO: 7 |
| Pmyo3-F | 5'-caaatttctcggcgatttgt, SEQ ID NO: 8 |

TABLE 2

RNA primers.

| | |
|---|---|
| bmk-1-F | 5'-cgaaagttgcggagaatcat, SEQ ID NO: 9 |
| bmk-1-R | 5'-ttcacatcgcaagtctccac, SEQ ID NO: 10 |
| hsp-16-F | 5'-ggctcagatggaacgtcaa, SEQ ID NO: 11 |
| hsp-16-R | 5'-gcttgaactgcgagacattg, SEQ ID NO: 12 |
| ced-3-F | 5'-cggagttcctgcatttcttc, SEQ ID NO: 13 |
| ced-3-R | 5'-acagacggcttgaatgaacc, SEQ ID NO: 14 |
| hsp-70-F | 5'-tgaaaaggcacttcgtgatg, SEQ ID NO: 15 |
| hsp-70-R | 5'-ccaaaggctactgcttcgtc, SEQ ID NO: 16 |
| hsp-12-F | 5'-gtgatggctgacgaaggaac, SEQ ID NO: 17 |
| hsp-12-R | 5'-gggaggaagttatgggcttc, SEQ ID NO: 18 |
| act-1-F | 5'-tgctgatcgtatgcagaagg, SEQ ID NO: 19 |
| act-1-R | 5'-tagatcctccgatccagacg, SEQ ID NO: 20 |

Examination of the expression of pch-2 homologs in mouse and human tissues. Total RNA from mouse and human ovaries were isolated with the RNeasy mini kit (QIAGEN, Venlo, Limburg). Five young animals (3 months old) and 5 older animals (22 months old) were used for the gene expression analysis. Eight young humans (ages 18-25 yrs old) and 10 older humans (ages >60 yrs old) were included for this study. Gene expression was analyzed by Affymetrix gene array (version ST 1.0) and the differential expression of pch-2 homologs was judged by both fold change and by p value.

Examination of the expression of bmk-1 homologs in mouse and human tissues. Total RNA of mouse and human ovaries were isolated with the RNeasy mini kit (QIAGEN). Five young animals (3 months old) and 5 old animals (22 months old) were used for the gene expression analysis. Eight young humans (ages 18-25 yrs old) and 10 old humans (ages >60 yrs old) were included for this study. Gene expression was analyzed by Affymetrix gene array (version ST 1.0) and the differential expression of Bmk-1 homologs was judged by both fold change and by p value.

Fibroblast cell culture. Normal human adult dermal fibroblast cells were purchased from ATTC (Manassas, Va.). Cell culture was maintained at 37° C., 5% CO2 in DMEM (Invitrogen, Carlsbad, Calif.) supplemented with 10% FBS and 100 u/ml penicillin-streptomycin.

Retroviral vector constructs. Human TRIP13 full length cDNA was amplified from a construct, pCMV6-XL5-TRIP13 (Origene, Rockville, Md.), by PCR using two cloning site tagged primers hTRIP13-1F and hTRIP13-1R (see Table 3) and cloned into SalI and BamHI sites of pBABEhygro-hTERT (Cell Biolabs, San Diego, Calif.). The insert was confirmed by sequencing. Control empty vector, pBABE-hygro, was from Addgene. (Cambridge, Mass.).

Transfection and cell infection. Retroviruses were produced by transfection of the retroviral constructs in the Platinum-A Retroviral packing cell line (Cell Biolabs, San Diego, Calif.). Briefly, Plat-A cells were grown to 70% confluency in 10-cm dishes with DMEM, 10% FBS without antibiotics and transiently transfected with Lipofectamine (Invitrogen, Carlsbad, Calif.). Purified 10 µg plasmid DNA of pBABEhygro-hTRIP13 was mixed with Lipofectamine 2000 transfection reagent 30 µl in Opti-MEM according to the manufacturer's protocol and was incubated overnight, then the media was exchanged with growth medium without antibiotics. After 48 hours of infection, retroviral supernatants were collected after brief centrifugation at 1200 rpm for 5 minutes. Empty vector pBABEhygro was packaged in parallel as a control.

Human dermal fibroblast cells were grown to 50% confluency and infected with retrovirus in growth medium at a ratio 1:1 for two overnight doses in the presence of 10 µg/µl polybrene. After 72 hours of infection, the infected cells were selected and maintained in growth medium with 90 µg/ml hygromycin to obtain a stable line. Wild type (WT) was uninfected fibroblast cells treated the same as the infected lines for the controls. An empty vector cell lines was generated by infection with pBABE-hygro without the transgene insert. The TRIP13 cell line was generated by infection with pBABEhygro-TRIP13.

Cell Culture Stresses:

1) $H_2O_2$ treatment. Cells were plated in 6-well plates for 24 h and replaced with growth medium containing 600 µM $H_2O_2$ and incubated for 2 h. Then the media was replaced with growth medium and incubated for 4 days. Cells were trypsinized and split at a 1:2 ratio in 6-well plates and incubated for 24 h. Cells were treated for a second time with $H_2O_2$ for 2 h and then grown with growth medium for 24 h.
2) Etoposide treatment. Etoposide (Sigma, St. Louis, Mo.) was dissolved in $Me_2SO$ and added to growth medium at a final concentration of 10 µM. Cells were plated in 6-well plates for 24 h and incubated with growth medium and etoposide for 3 days. Growth medium with $Me_2SO$ and not etoposide was a control.
3) UVC radiation. Cells were plated in 6 well plates for 24 h and medium was replaced with PBS. Cells were put in a crosslinker (UVP, Upland, Calif.) for UVC exposure at 50 $J/m^2$. Then cells were grown in growth medium and incubated for 24 h.
4) Cell counting. Cells were washed with PBS and trypsinized with 0.25% trypsin for 5 minutes. Cells were diluted in growth medium and mixed with equal volumes of trypan blue. 20 µl of mixture was loaded into a counting chamber and counted by Cellometer Auto T4 Cell Counter. (Nexcelom Bioscience, Lawrence, Mass.). All cells were counted 24 hours after administration of the final stress condition. For all experiments, cell stresses were performed on triplicate cultures (n=3).

RNA isolation and Quantitative PCR. Total RNA was isolated using RNeasy mini kit from QIAGEN (Valencia, Calif.).

For cells: Cell plates were washed with PBS twice and resuspended in 350 µl lysis buffer with β-mercaptoethanol.

For worms: 10 adult worms per sample were washed in M9 buffer three times and excess M9 was carefully removed.

The samples were resuspended in 350 µl lysis buffer with β-mercaptoethanol. Equal volume of 70% ethanol was mixed with the lysis buffer. The mixtures were transferred to spin columns and followed by washing steps according the manufacturer protocol. DNase digestion was performed in the column and RNA was eluted in RNase-free water (25 µl in cell samples and 13 µl in worm samples). 1 µg cell RNA or 12 µl worm RNA was used to synthesize cDNA with an Ominscript kit (QIAGEN). For real-time PCR, each 25 µl reaction contained 12.5 µl of 2× SybrGreen supermix (Bio-Rad), 0.4 µM of each primer hTRIP13-2F, hTRIP13-2R; hGAPDH-F, hGAPDH-R; pch-2-1F, pch-2-1R; sir-2.1-F, sir-2.1-R; or act-1-F, act-1-R (See Table 3) and 2 µl of template cDNA. Rt-PCR was performed on a C1600 Thermal Cycler (Bio-Rad, Waltham, Mass.). Relative gene expression levels were normalized to GAPDH or act-1 and calculated using the ΔΔCt (cycle threshold) method.

TABLE 3

Primers used.

Primers were used for studies: Cloning primers

| | |
|---|---|
| hTRIP13-1F | 5'-gtattaaggatcctacgtaatggacgaggccgtgg, SEQ ID NO: 21 |
| hTRIP13-1R | 5'-acagggtcgactcagatgtaagctgcaag, SEQ ID NO: 22 |
| attB1-gfp-F | 5'-ggggacaagtttgtacaaaaaagcaggctcgttcaccatgagtaaaggagaa, SEQ ID NO: 23 |

TABLE 3-continued

Primers used.

| | |
|---|---|
| attB2-gfp-R | 5'-ggggaccactttgtacaagaaagctgggtccagcggccgatgttagttagtta, SEQ ID NO: 24 |
| attB1-pch-2-F | 5'-ggggacaagtttgtacaaaaaagcaggctcgtcagactaaagtatgcacgag, SEQ ID NO: 25 |
| attB2-pch-2-R | 5'-ggggaccactttgtacaagaaagctgggtctaaaatttaattatttctact, SEQ ID NO: 26 |
| attB4-Pmyo3-F | 5'-ggggacaactttgtatagaaaagttgaacggctataataagttctt, SEQ ID NO: 27 |
| attB1r-Pmyo3-R | 5'-ggggactgcttttttgtacaaacttgttctagatggatctagtgg, SEQ ID NO: 28 |
| pch-2-R | 5'-gatgatgaggattcacgacaca, SEQ ID NO: 29 |
| Pmyo3-F | 5'-caaatttctcggcgatttgt, SEQ ID NO: 30 |
| mRNA primers | |
| hTRIP13-2F | 5'-tgtgtaaagcgttagcccaga, SEQ ID NO: 31 |
| hTRIP13-2R | 5'-gccactttccgaaaaccactta, SEQ ID NO: 32 |
| hGAPDH-F | 5'-ccactcctccacctttgacg, SEQ ID NO: 33 |
| hGAPDH-R | 5'-catgaggtccaccaccctgt, SEQ ID NO: 34 |
| pch-2-1F | 5'-ggaagccaatttcgtctgtc, SEQ ID NO: 35 |
| pch-2-1R | 5'-ccccatctctgagttcacaag, SEQ ID NO: 36 |
| sir-2.1-F | 5'-tccgacagcaatgttcgata, SEQ ID NO: 37 |
| sir-2.1-R | 5'-tttcgaagaagacgaccagaa, SEQ ID NO: 38 |
| act-1-F | 5'-tgctgatcgtatgcagaagg, SEQ ID NO: 39 |
| act-1-R | 5'-tagatcctccgatccagacg, SEQ ID NO: 40 |

Western Blot. Cell plates were washed with PBS twice and scripted with RIPA buffer (Boston BioProducts, Ashland, Mass.) and protease inhibitor cocktail (Roche, Indianapolis, Ind.). The protein supernatants were collected after centrifuging at 10000 rpm for 20 min at 4 °C. and measured using a PierceBCA Protein Assay Kit (Thermo scientific, Rockford, Calif.). Protein samples (30 μg) were subjected to 10% SDS-PAGE and transferred to a polyvinylidene fluoride (PVDF)-membrane (Bio-Rad, Waltham, Mass.). The membrane was blocked with 5% BSA for 1 h at room temperature and was incubated with primary antibodies, rabbit anti-TRIP13(~49 kDa) (Abcam, Cambridge, Mass.); or mouse anti-β-Actin (~42 kDa) (Abcam) overnight at 4 °C. Corresponding HRP-labeled secondary antibody was incubated with the membranes at room temperature for 1 hr. All signal bands were quantified by ImageJ software.

Fibroblast cell culture. Human normal adult dermal fibroblast cells were purchased from ATTC (Manassas, Va.). Cell culture was maintained at 37° C., 5% $CO_2$ in DMEM (Invitrogen, Grand Island, N.Y.) supplemented with 10% FBS and 100 U/ml Penicillin-Streptomycin.

Retroviral vector constructs. Human full length cDNA for TRIP13 and KIF11 (human homologs of the PCH-2 and BMK-1 genes, respectively) was amplified from construct pCMV6-XL5-TRIP13 (Origene, Rockville, Md.) by PCR, and cloned into SalI and BamHI sites of pBABEhygro-hTERT (Cell Biolabs, San Diego, Calif.). The inserts were confirmed by sequencing. Control empty vector pBABE-hygro was from Addgene. (Cambridge, Mass.).

Transfection and cell infection. Retroviruses were produced by transfection of the retroviral constructs in the Platinum-A Retroviral packing cell line (Cell Biolabs). Briefly, Plat-A cells were grown to 70% confluency in 10-cm dishes with DMEM, 10% FBS without antibiotics and transiently transfected with lipid transfection reagent, LIPOFECTAMINE® (Invitrogen, Carlsbad, Calif.). Purified 10 μg plasmid DNA of pBABEhygro-hTRIP13 was mixed with 30 μl LIPOFECTAMINE 2000® transfection reagent in Opti-MEM, according to the manufacturer's protocol, and were incubated overnight, then exchanged with growth medium without antibiotics. After 48 hours of infection, retroviral supernatants were collected by brief centrifugation at 1200 rpm for 5 minutes. Empty vector pBABEhygro was packaged in parallel as control.

Human dermal fibroblast cells were grown to 50% confluency and infected by retrovirus with growth medium at ratio 1:1 for 2 doses of overnight in the presence of 10 μg/μl polybrene. After 72 hours of infection, the infected cells were selected and maintained in growth medium with 9 μg/ml hygromycin to obtain a stable line. Wild type (WT) was uninfected fibroblast cells at the same passage number of infected lines as one of the controls. Empty vector cell line was generated by infection with pBABE-hygro without the transgene insert. The TRIP13 and KIF11 cell lines were generated by infection with pBABEhygro-TRIP13 and pBABEhygro-KIF11, respectively.

Cell Culture Stresses.

1) $H_2O_2$ treatment—oxidative stressor. Cells were plated in 6-well plates for 24 h and replaced by growth medium with 600 µM $H_2O_2$ and incubated for 2 hours. Then cells were exchanged back into growth medium and incubated for 4 days. Cells were trypsinized and split at a 1:2 ratio in 6-well plates and incubated for 24 hours. Cells were treated for a second time with $H_2O_2$ for 2 hour and then were replaced with growth medium for 24 hours.

2) Etoposide treatment—induces DNA strand breaks. Etoposide (Sigma, St. Louis, Mo.) was dissolved in $Me_2SO$ and added to growth medium at a final concentration of 10 µM. Cells were plated in 6-well plates for 24 hours and the media was replaced with growth medium and etoposide for 3 days. Growth medium with $Me_2SO$ only (no etoposide) was used as a control.

3) UVC radiation—DNA damage. Cells were plated in 6 well plates for 24 hours and the media was replaced with medium and PBS. Cells were put in a crosslinker (UVP, Upland, Calif.) for UVC exposure at 50 $J/m^2$. Then cells were placed back in growth medium and incubated for 24 hours.

4) Cell counting. Fibroblasts were washed with PBS and trypsinized with 0.25% trypsin for 5 minutes. Cells were diluted in growth medium and mixed with an equal volume of trypan blue, and 20 µl of the mixture was loaded into a counting chamber and counted by an automated cell counter (Cellometer Auto T4 Cell Counter, Nexcelom Bioscience, Lawrence, Mass.).

All cells were counted 24 hours after administration of the final stress for that condition. For all experiments, cell culture stress experiments were performed on triplicate cultures (n=3).

The Results of the experiments disclosed herein are now described.

Example 1

PCH-2 Regulates the Lifespan of *C. elegans*

To study the evolutionary conservation of pch-2, protein sequences of PCH-2 and its homologs among various species were first examined using the NCBI RefSeq database. A phylogenetic analysis was performed using Phylogeny.fr, and the protein sequence alignments of PCH-2 and its homologs were evaluated. PCH-2, similar to Sir2, is an evolutionarily conserved gene with a P-loop_NTPase functional domain, found across species including yeast (*S. cerevisiae*), worm (*C. elegans*), fly (*D. melanogaster*), zebrafish (*D. rerio*), rodent (*R. novegicus, M. musculus*) and human (*H. sapiens*) (FIG. 1A and Table 4). Interestingly, the meiotic checkpoint function of PCH-2 and its homologs have been studied not only in yeast, but also in worms and mice. Collectively, these findings provide evidence for evolutionarily conserved functions for PCH-2 in both recombination, and the formation of higher order chromosome structures. PCH-2 may provide some fundamental function across the animal kingdom.

TABLE 4

Homologs of PCH-2

| Gene Symbol | Gene Accession No. | Species |
| --- | --- | --- |
| PCH2 | NP_009745 | *Saccharomyces cerevisiae* |
| pch-2 | NP_495711 | *Caenorhabditis elegans* |

TABLE 4-continued

Homologs of PCH-2

| Gene Symbol | Gene Accession No. | Species |
| --- | --- | --- |
| pch2 | NP_001287235 | *Drosophila melanogaster* |
| trip13 | NP_956876 | *Danio rerio* |
| Trip13 | NP_081458 | *Mus musculus* |
| Trip13 | NP_001011930 | *Rattus norvegicus* |
| TRIP13 | XP_851775 | *Canis lupus familiaris* |
| AT4G24710 | NP_194202 | *Arabidopsis thaliana* |
| TRIP13 | NP_001159732 | *Homo sapiens* |

Note:
Gene Symbols and Gene Accessible Numbers are from RefSeq database of National Center for Biotechnology Information, NIH.

To evaluate expression of pch-2 homologs in mammalian species, brain and gonadal tissues from mouse and human samples were examined. pch-2 is known to be involved in preventing meiotic interhomolog recombination. Expression levels of a pch-2 homolog, TRIP13, was measured in young subjects (N=5 for 3 month-old mice from two aging colonies, C57B/6 and DBA2; N=8 for 18-25 year-old humans) and older subjects (N=5 for 22 month-old for mice, from two aging colonies; and N=10 for >60 year-old humans). Expression was found to decline significantly with physiological aging in ovary and brain tissues of both human and mouse (FIG. 1B). This was judged by both fold change in mRNA expression, as well as by p-value changes in mouse and human tissues. It was also observed that a clear trend the pch-2 expression decreased in *C. elegans* over the lifespan of the animals, from day 2 to day 21 (FIG. 1B). This observation suggested an evolutionarily conserved loss of expression of pch-2 with tissue aging, in *C. elegans*, mouse and human.

To investigate any potential role of the pch-2 gene family in lifespan and stress resistance, a human pch-2 homolog—TRIP13—over-expression retroviral vector was first generated. This retrovirus was used to infect normal dermal human fibroblasts under hygromycin selection. TRIP13-over-expressing fibroblasts were compared to those infected with empty vector, as well as non-infected controls. After retroviral infection and hygromycin selection, it was found that doubling times for WT, empty vector, and TRIP13 over-expressing populations were 57 hours, 84 hours and 130 hours, respectively.

Figure 2B:
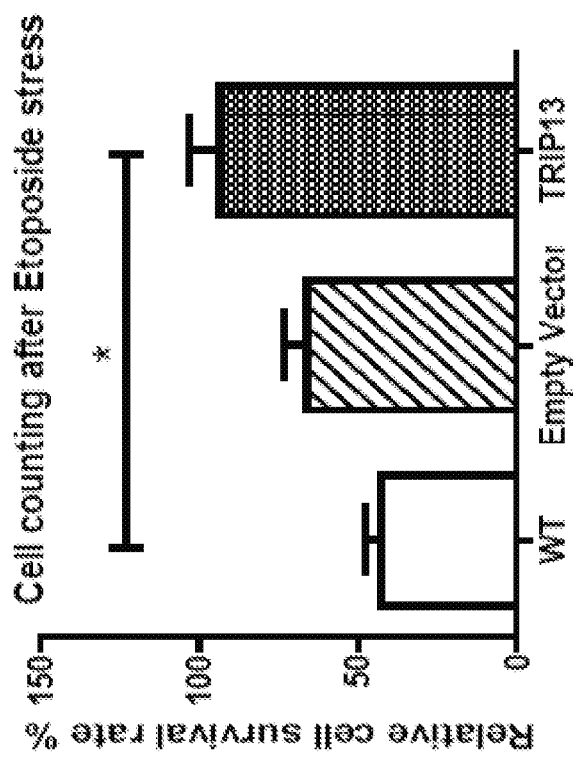
FIGS. 2A-2C, shows TRIP13 over-expression in human fibroblast cells conferred resistance to stressors of oxidation, apoptosis and DNA damage.
Figure 2A:
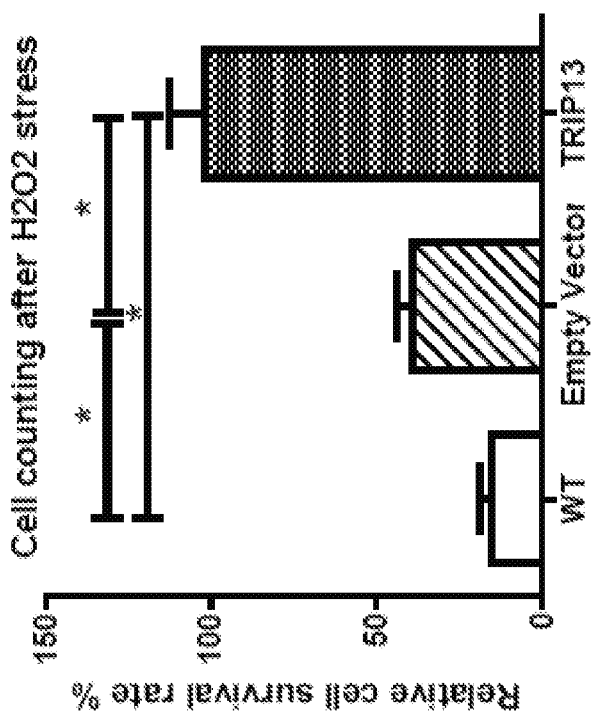
Figure 2C:
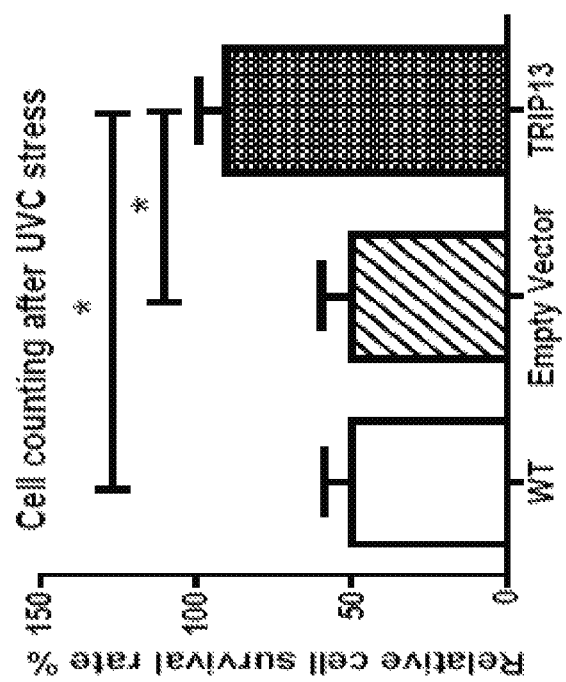

After populations were selected, environmental stressors 600 µM $H_2O_2$ (oxidative stress), 10 µM etoposide (apoptotic stress) and the UV radiation (DNA damage stressor) at 50 $J/m^2$ were applied. After 600 µM $H_2O_2$ treatment, the TRIP13 over-expressing populations showed significant enhancement of cell survival rates when compared to control groups, both the empty vector and WT (FIG. 2A, p<0.0001). When treated with 10 µM etoposide for 3 days, TRIP13 over-expressing cells also survived at a significantly higher rate (FIG. 2B, p<0.001). Similar results were observed in TRIP13 over-expressing populations after UV radiation as compared to the control groups (FIG. 2C, p<0.01). Since the population doubling times of TRIP13-transfected cells was slower than that of controls, this improved survival after application of stressors was thought to be more than an artifact of faster cell cycling. The results indicated that TRIP13 conferred an enhancement to fibroblast cell survival under various stressors of oxidation, apoptosis and DNA damage. All of these stressors are potentially involved in the normal aging process.

Based upon these observations, it was determined whetherpch-2 played a role in longevity. Given that lifespan in *C.*

Figure 8A:
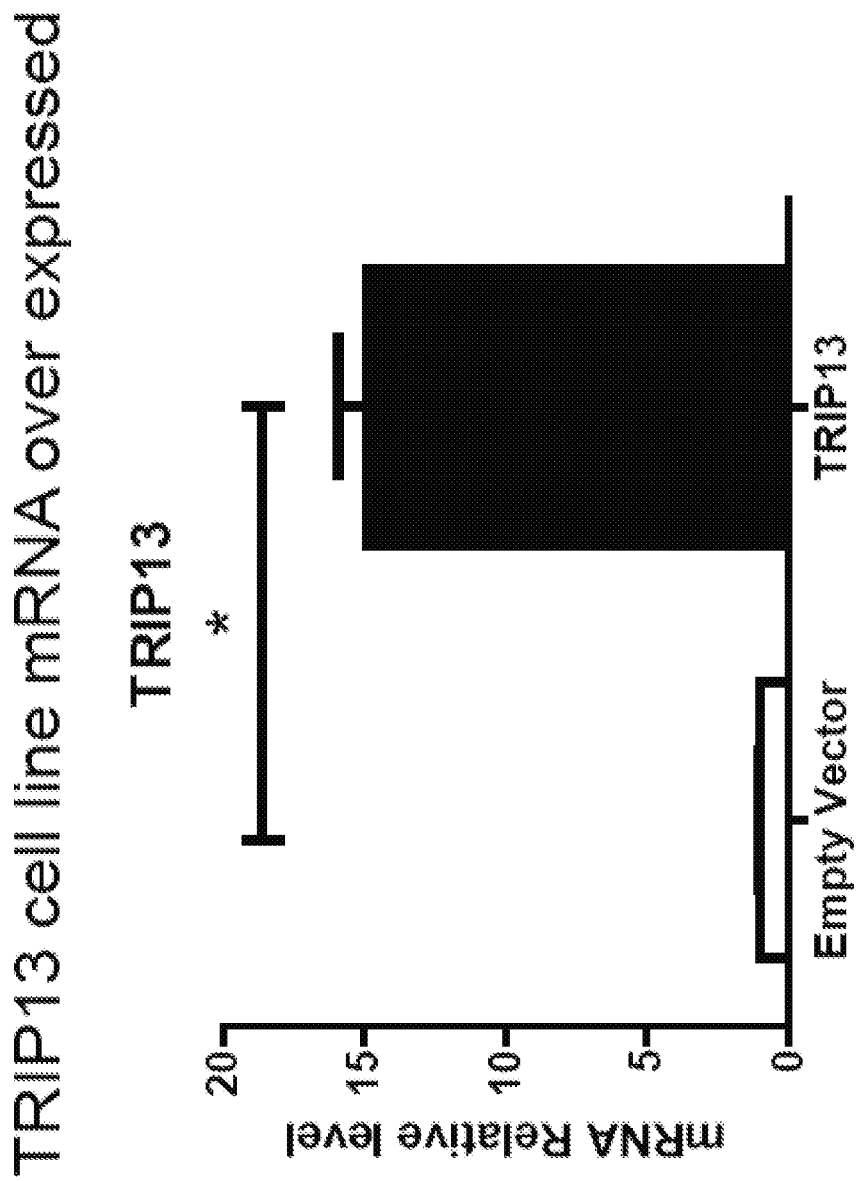
FIGS. 8A and 8B, is an illustration showing the establishment of TRIP13 over-expression in fibroblast cells.
Figure 8B:
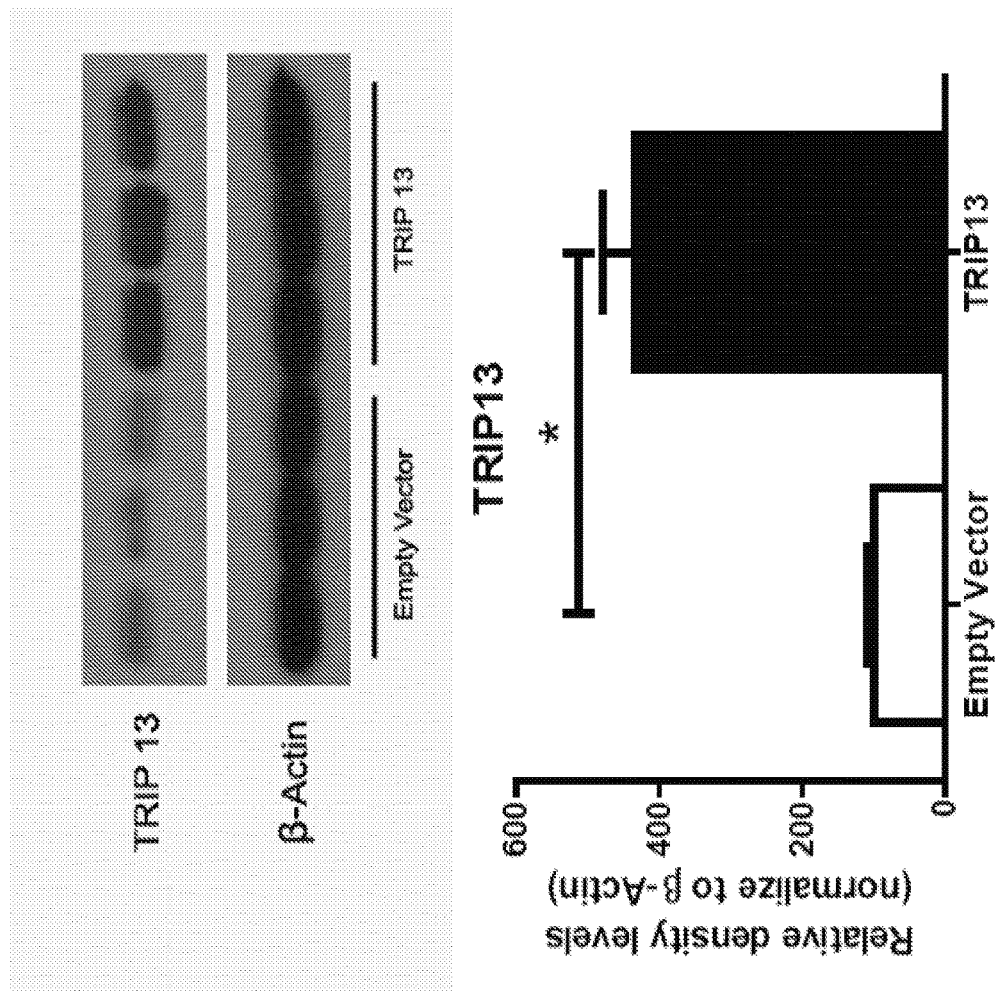
Figure 9:
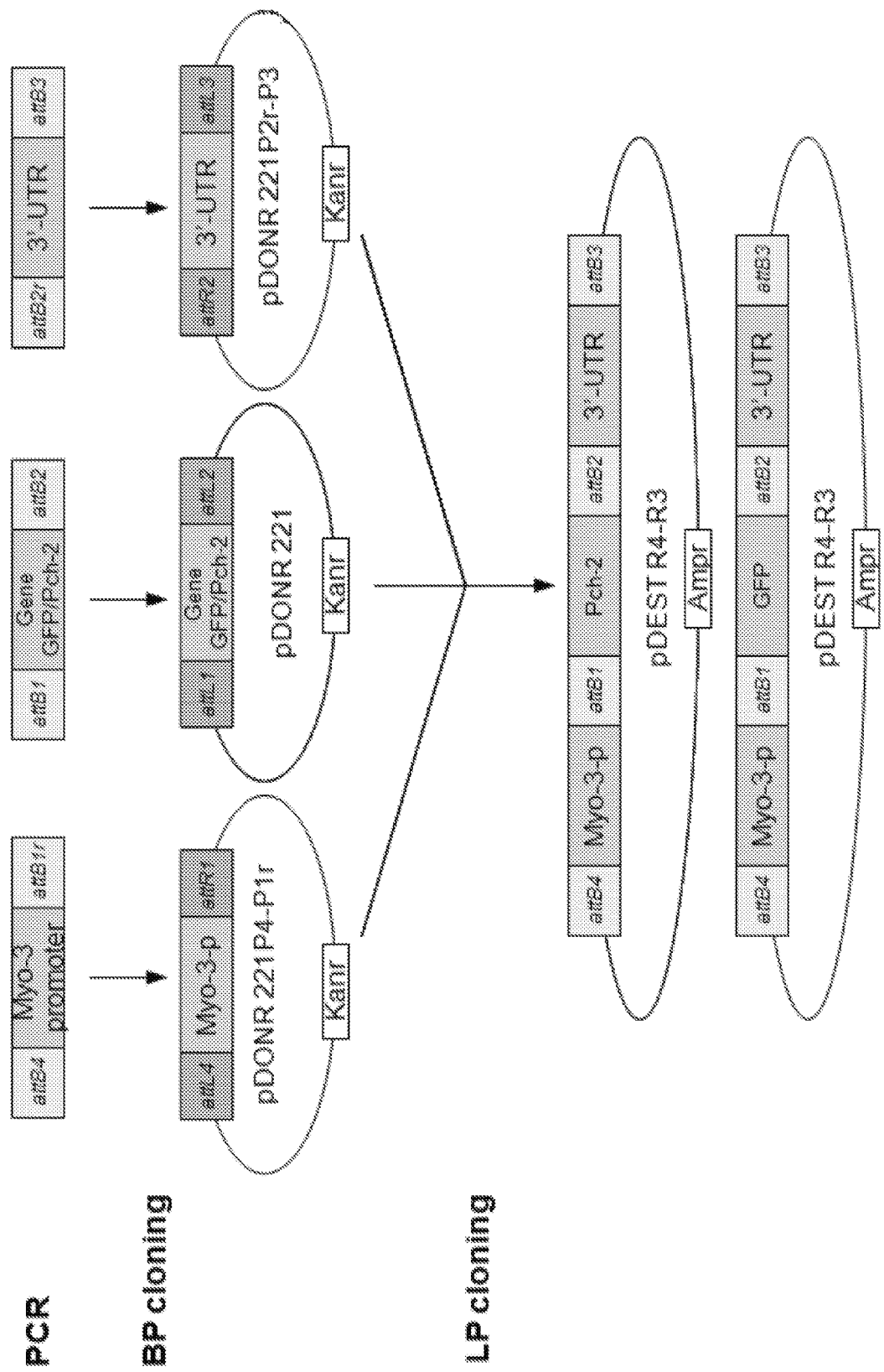
FIG. 9 is an illustration showing the construction of pch-2 and GFP plasmids.

*elegans* is only 3-4 weeks, as opposed to approximately 2-3 years in mice, the impact of the pch-2 gene on lifespan in *C. elegans* was examined. pch-2 over-expressing *C. elegans* lines were generated by a microinjection method (FIGS. 8A and 8B). The functional impact of pch-2 on worm longevity was studied. To identify over-expressingpch-2 lines, animals co-expressing GFP were selected by direct visualization. In GFP-expressing lines, the expression levels of pch-2 were also measured using quantitative reverse transcription polymerase reaction (qRT-PCR). The expression of endogenous and exogenous pch-2 was distinguished using an expression vector-specific primer and apch-2-specific primer.

Figure 3B:
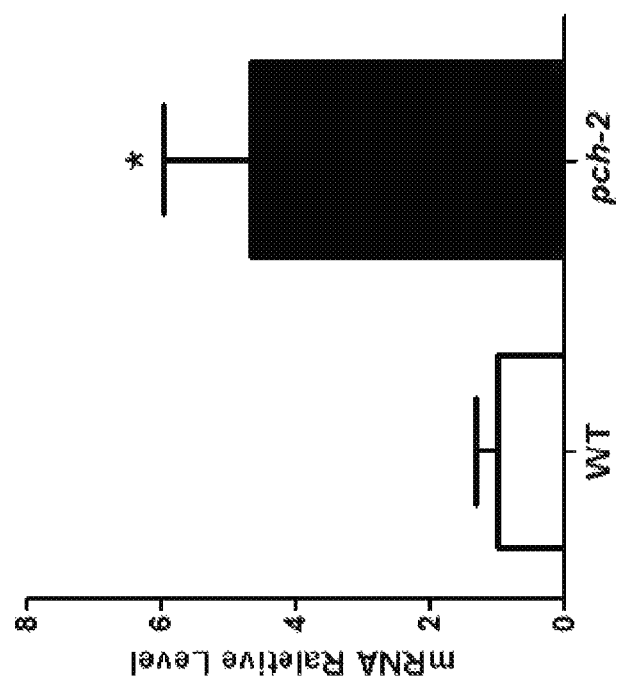
FIGS. 3A-3F, shows pch-2 over-expression extended lifespan and enhanced stress-resistance in C. elegans.
Figure 3A:
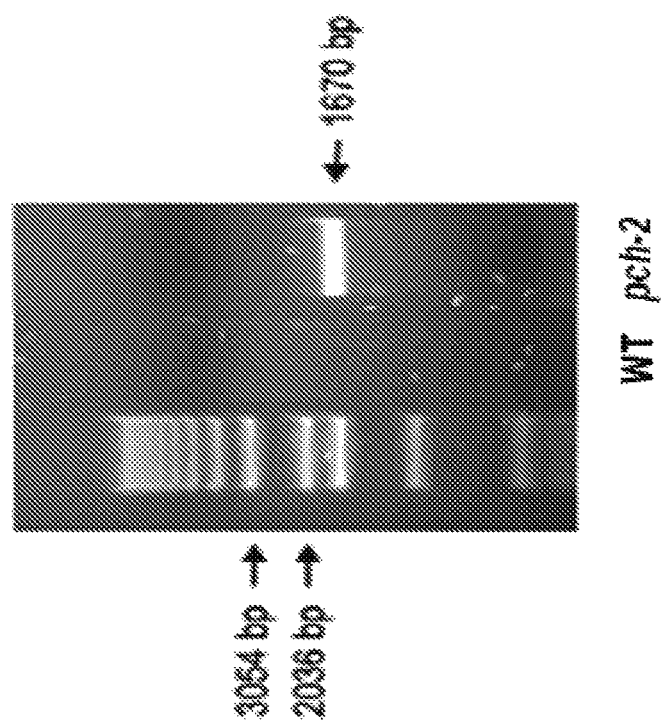
Figure 3C:
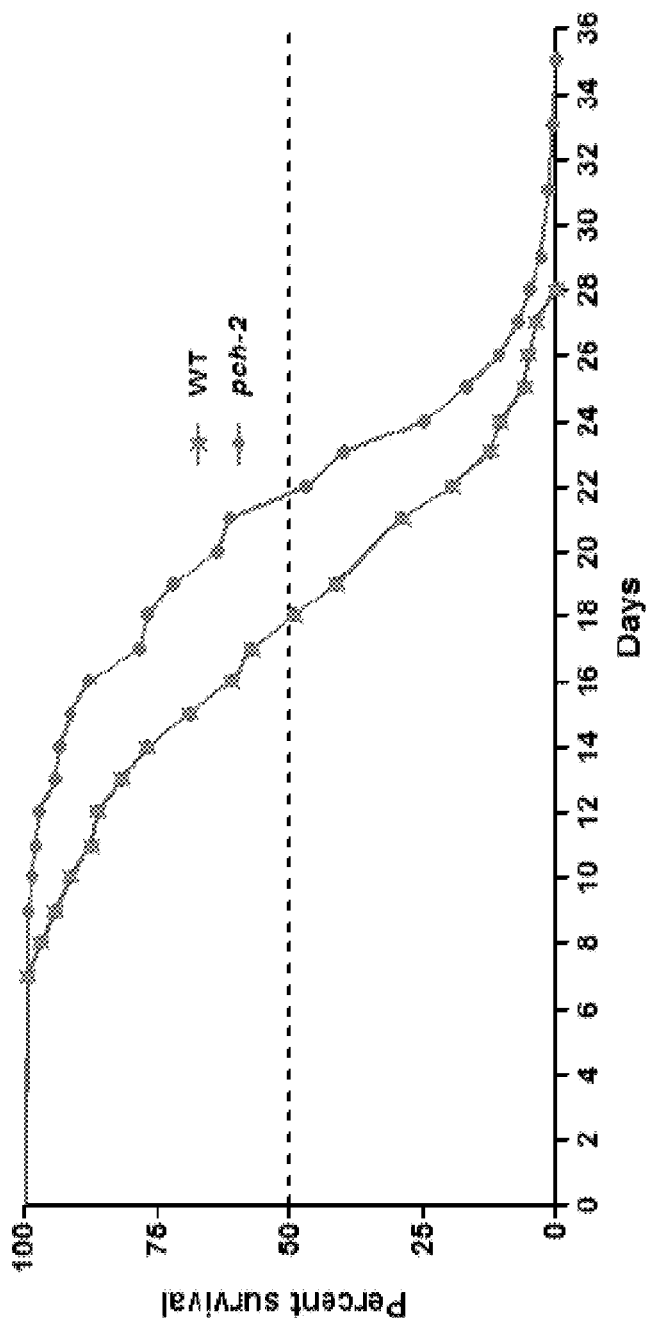

In GFP-positive over-expressing lines, the level of exogenous pch-2 expression was three times higher than the level of endogenous pch-2 in the wild-type (WT) controls (FIGS. 3A and 3B). After confirming over-expression, pch-2 over-expressing and WT worms were subjected to lifespan measurements. The median lifespans of WT and pch-2 over-expressers were 18 days and 22 days, respectively, with maximum lifespans of 28 days and 35 days, respectively (FIG. 3C). Hence, pch-2 over-expressing lines extended both median and maximum lifespans by approximately 25% as compared to WT (log rank test, n=126/140, p<0.001).

Figure 3D:
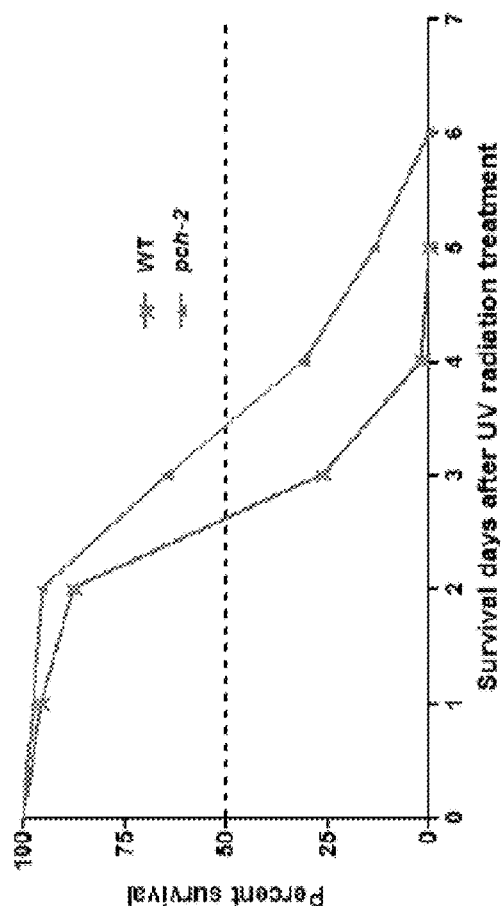

It was next determined whetherpch-2 over-expressing lines could withstand various stressors better than WT (GFP-expressing) controls. Young adult worms over-expressing pch-2 and controls were treated on day 1 with the oxidative stressor, 4 mM paraquat. The median survival of pch-2 over-expressing lines was 5.6 days, while that of control lines was 4.0 days. The maximum survival of pch-2 over-expressing and WT lines were 15 days and 6 days, respectively, which was an increase of 40% and 150% in median and maximal survival for pch-2 over-expressers (p<0.001 for both median and maximal survival as compared to WT controls by log rank test) (FIG. 3D).

Figure 3E:
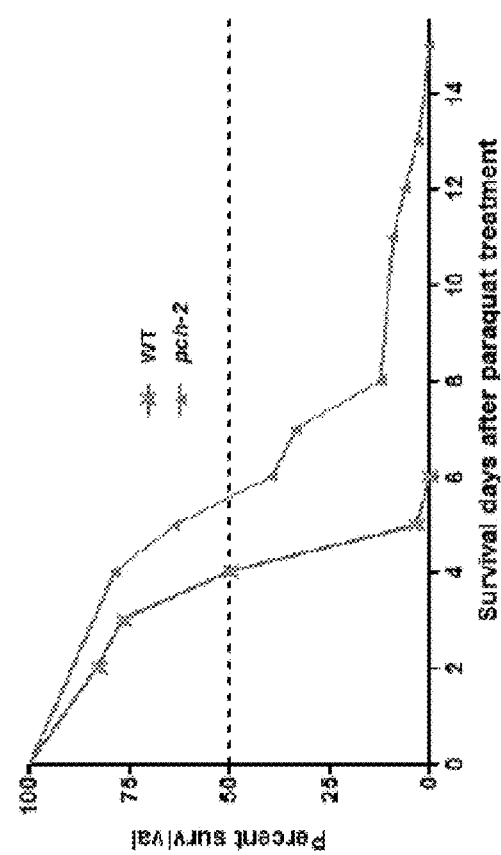
Figure 3F:
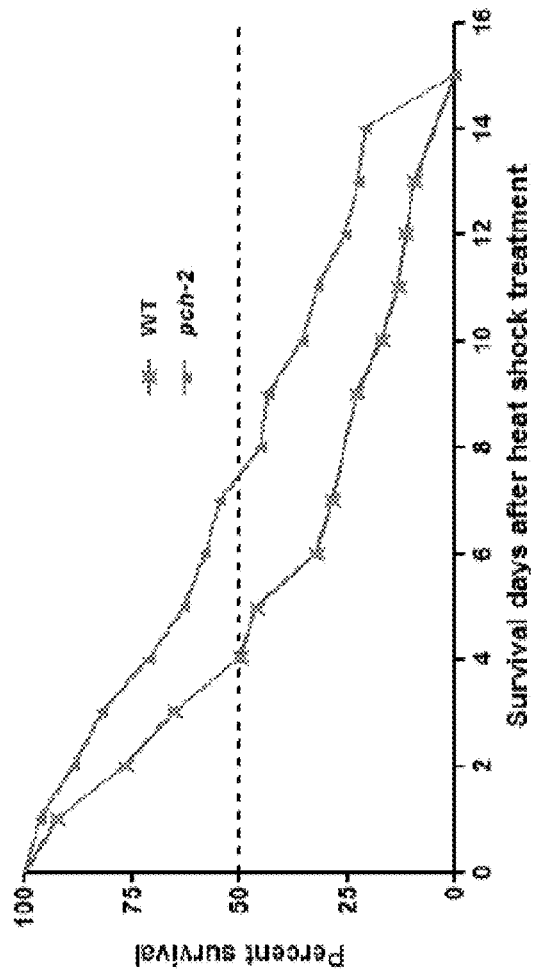

Day 1 worms were also exposed to DNA damage, UV radiation at 0.1 J/cm2. The median survival of pch-2 over-expressing lines was 3.4 days and control lines was 2.6 days after UV radiation. The maximum survival was 6 days and 5 days, respectively (45% and 20% higher for pch-2, respectively, p<0.001) (FIG. 3E). Lastly, heat shock was administered on day 1 to worms, 35° C. for 2 hours, after which animals were removed to routine conditions and their survival was tallied. Intriguingly, the median survival of pch-2 over-expressing lines was 85.0% longer than that of control lines (7.4 days vs. 4 days) (p<0.0001), but the maximum survival was not changed between the two lines (FIG. 3F). Hence, pch-2 conferred significantly increased resistance to multiple stressors which affected both DNA and protein integrity.

Figure 4B:
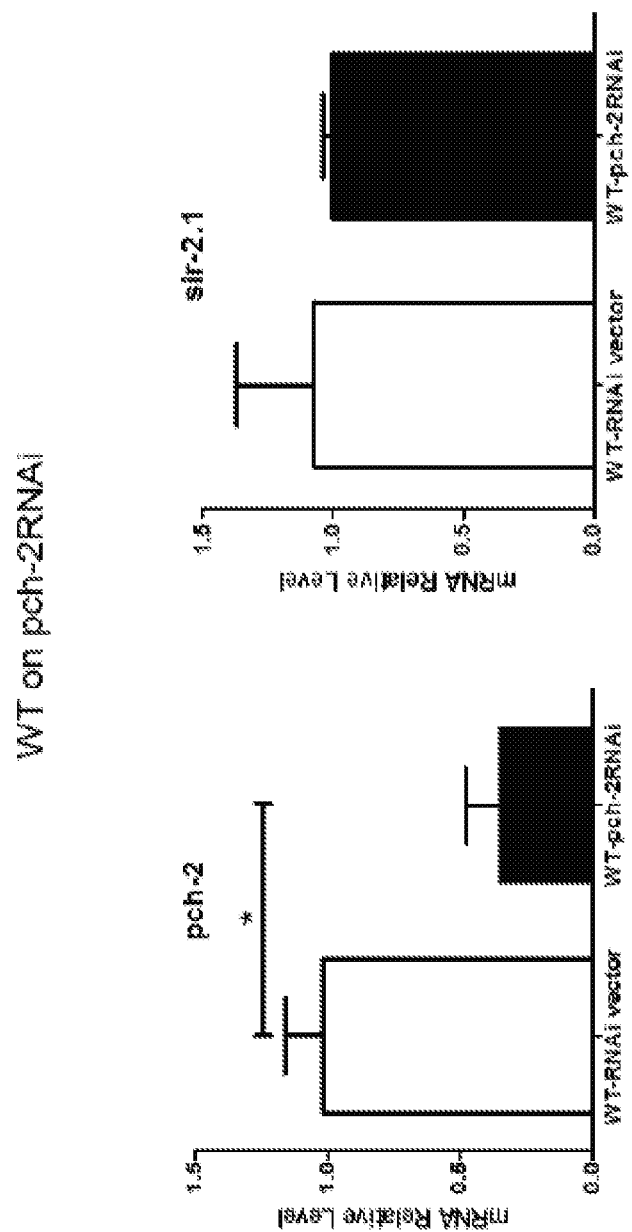
Figure 4C:
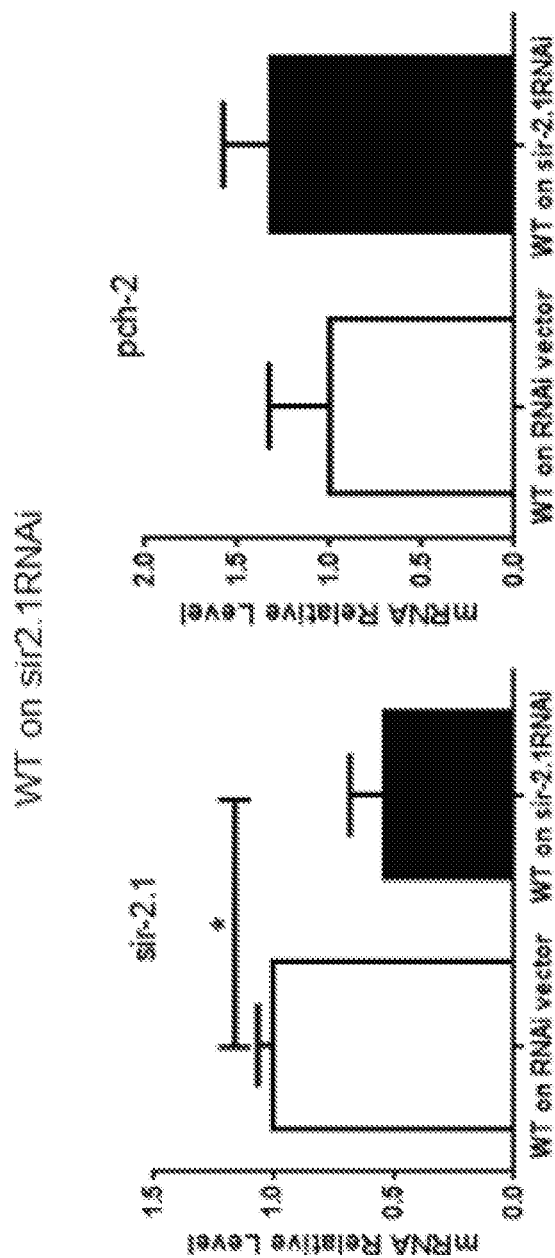

As further confirmation to the observations, lifespan after RNAi-inducedpch-2 and sir-2 knockdown was examined in WT N2 animals. A pch-2 specific RNAi clone F10B5.5 and a sir-2 specific RNAi clone T27E4.8 were used to feed WT N2 worms, thereby reducing pch-2 and sir-2 expression. The median lifespan of RNAi vector animals was 17 days, but was shortened to 10.5 days afterpch-2 RNAi treatment. Maximum lifespan was shortened to 19 days from 27 days, and both median and maximum lifespan were significantly shortened afterpch-2 RNAi treatment (p<0.0001) (FIG. 4A). Interestingly, similar results were obtained from RNAi inhibition of sir-2 in WT N2 animals (FIG. 4A). Only one-third expression of pch-2 and sir-2 remained after RNAi treatment, as assessed by qRT-PCR (FIGS. 4B and 4C). Furthermore, RNAi treatment was specific, and treatment of worms with pch-2 RNAi did not impact transcript levels for sir-2, for example. Hence, knockdown of sir-2 and pch-2 resulted in similar decrements in lifespan in WT worms.

Figure 5A:
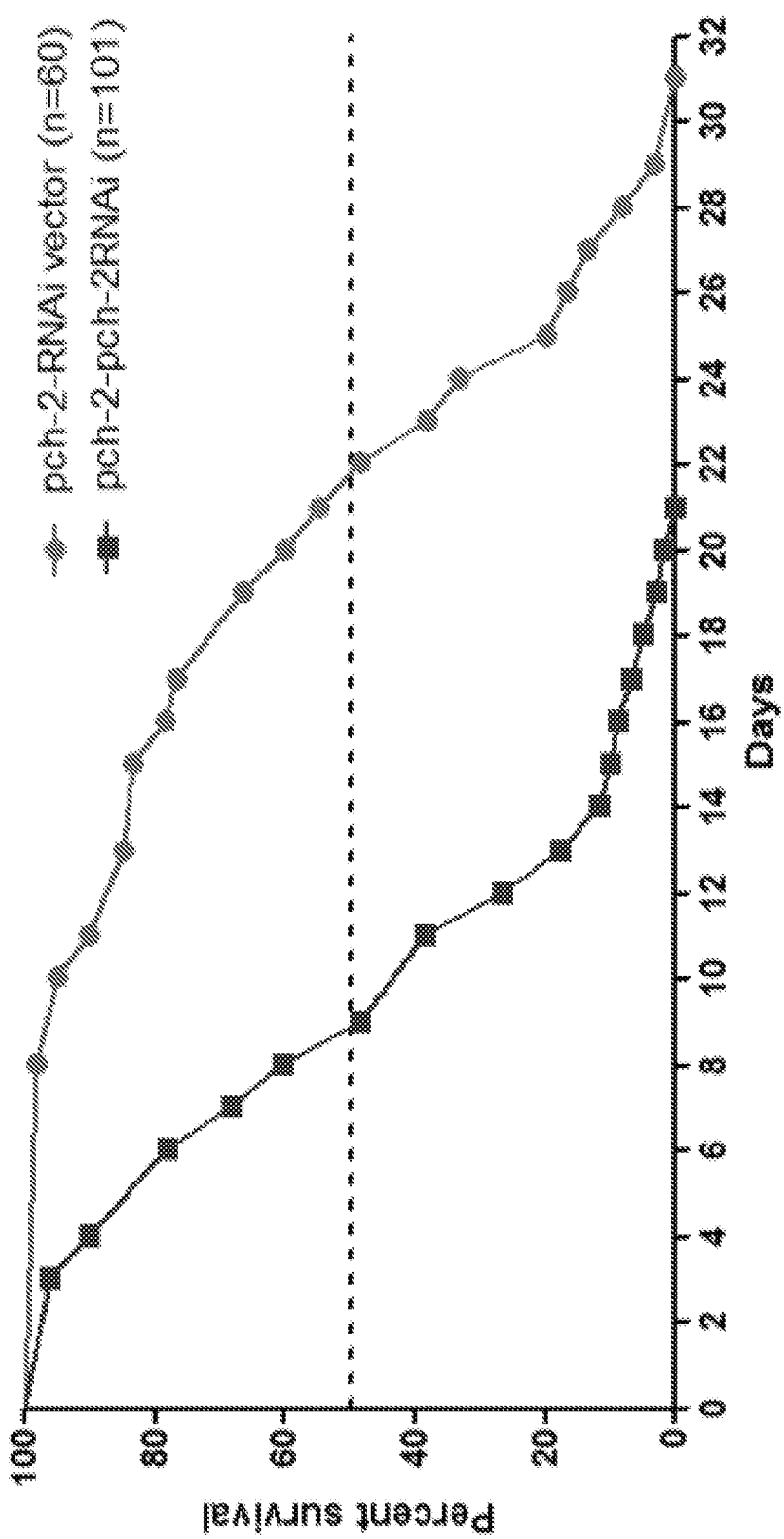
FIGS. 5A and 5B, shows the inhibition of pch-2 by RNAi impacted lifespan of pch-2 over-expressing C. elegans.
Figure 5B:
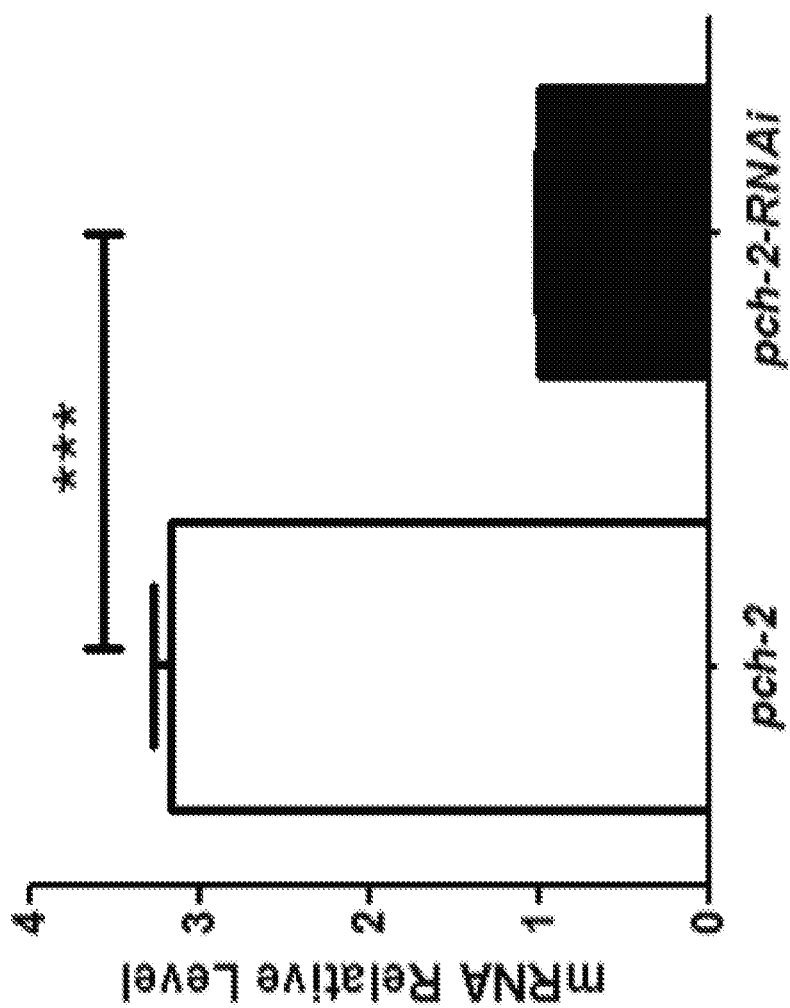

In addition, the lifespan of pch-2 over-expressing worm lines was evaluated when subjected to pch-2 RNAi treatment. The median lifespans of pch-2 RNAi and pch-2 over-expressers were 7 days and 23 days, respectively, with maximum lifespans of 20 days and 36 days, respectively (FIG. 5). Hence, pch-2 RNAi inhibition in pch-2 over-expressing lines shortened both median and maximum lifespan significantly when compared to pch-2 over-expressing worms (log rank test, p<0.0001).

Figure 6A:
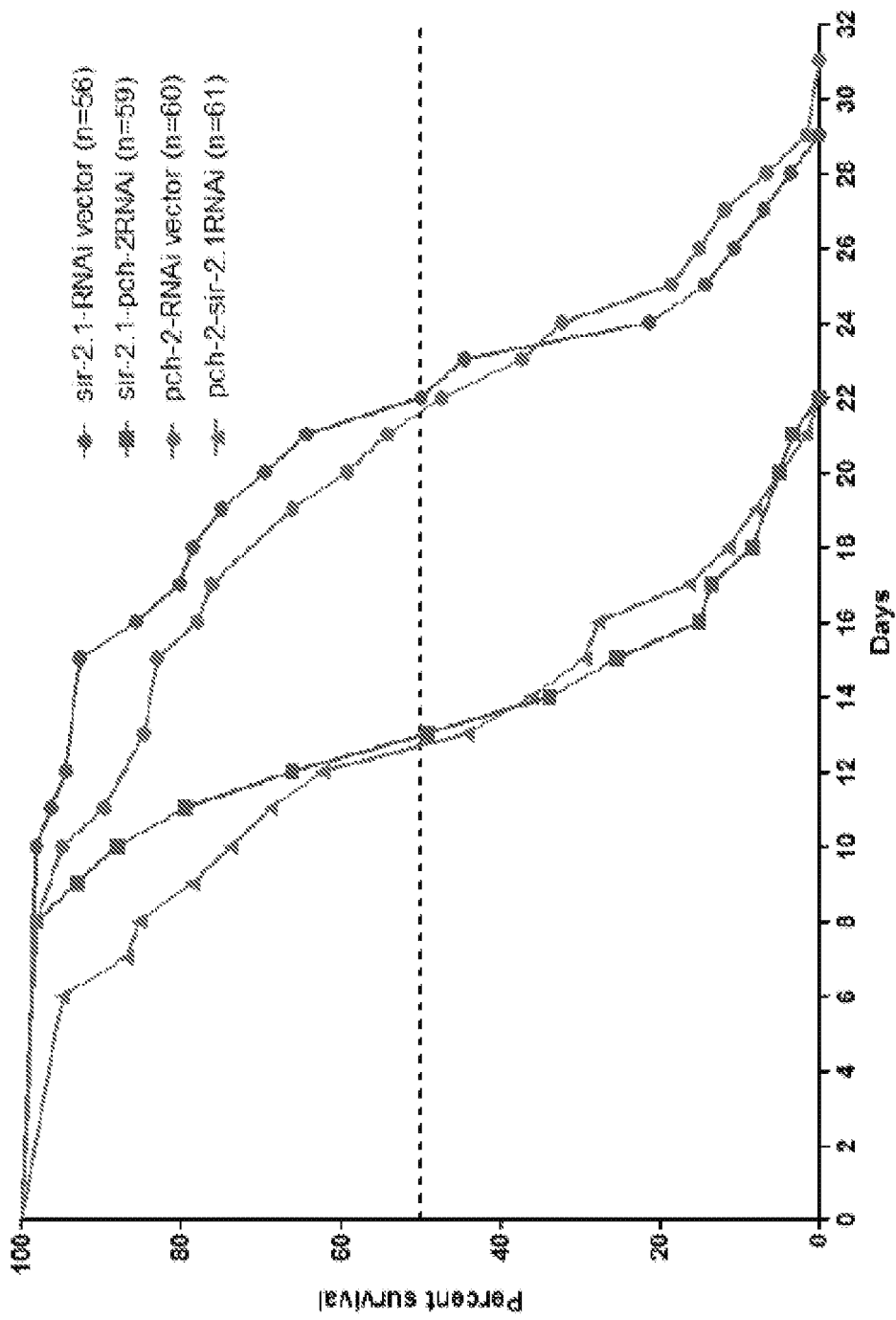

To further investigate the role of pch-2 in worm longevity, it was determined if pch-2 and sir-2 may have functional connections in worm lifespan determination. Therefore, the lifespan of pch-2 over-expressing worm lines with sir-2 RNAi treatment. The sir-2 longevity worm line (LG394 from CGC) was subjected to pch-2 RNAi treatment. The median lifespans of sir-2 longevity animals subjected to pch-2 RNAi and the sir-2 longevity line were 14 days and 23 days, with maximum lifespans of 22 days and 29 days, respectively (FIG. 6A). The median lifespans of pch-2 over-expressers exposed to sir-2 RNAi and the untreated pch-2 over-expressers were 14 days and 23 days, respectively, with maximum lifespans of 22 days and 31 days, respectively (FIG. 6A). Hence, pch-2 RNAi inhibition in the sir-2 longevity line and sir-2 RNAi inhibition in pch-2 over-expressing lines shortened both median and maximum lifespans by a similar amount (log rank test, p<0.0001 for both lines) (FIGS. 6A-6C).

qRT-PCR confirmation of the impact on the transcript levels of pch-2 and sir-2 RNAi showed clear effects on pch-2 and sir-2 inhibition (FIGS. 6B and 6C), confirming that RNAi treatment knocked down the target transcripts. However, there were no observed cross-over effects of either RNAi administrations on the other gene (FIGS. 6B and 6C). These genetic epistasis studies showed thatpch-2 and sir-2 operated independently and reciprocally to extend lifespan of worms, and that expression level of one gene did not appear to directly impact expression level of the other gene.

Classic genetic and functional genomics screens have identified a number of genes that are involved in *C. elegans* lifespan regulation. Dozens of single-gene mutations have been demonstrated to lead to worm lifespan extension of 20% or more. Many of these genes are components or downstream targets of the Insulin/IGF-1 and TOR signaling pathways. Reducing the expression of most of these genes by RNAi, for example, increases worm lifespan.

There are a small proportion of the insulin/IGF-1 pathway downstream key mediators, such as, DAF-16, SKN-1 and DAF-16-regulated genes including HSF-1 and RPN-6, that extend worm lifespan in over-expressors. pch-2, however, is not known to be involved with either the Insulin/IGF-1 or the TOR pathways. In current studies, over-expression of TRIP13, the human homolog of pch-2, in human fibroblasts exhibited enhanced resistance to environmental detrimental stressors, such as oxidative stress, apoptosis and UV radiation. The cells that over-expressed Trip13 had a slower proliferation rate than controls, meaning that increased proliferation in Trip13 over-expressors did not account for observed increases in cell number after stress.

Furthermore, over-expression of pch-2 in *C. elegans* led to increased lifespan, thereby suggesting that pch-2 was protective against worm aging. Conversely, decreasing pch-2 expression with RNAi led to a decrease in lifespan. The mechanism by which pch-2 enhanced lifespan may be independent of the widely-studied Insulin/IGF-1 and TOR pathways, but may possibly be related to mechanisms by which the sirtuins increase lifespan, given that inhibition of both pch-2 and sir-2 decreased lifespan by similar amounts and their spatial co-localization in the nucleoli. Since the expression of Trip13 declined with mammalian tissue aging (FIGS. 1A and 1B), these data suggest thatpch-2 (mammalian Trip13) may play an important role in the aging process.

These studies suggest that the anti-aging effects of sir-2 and the sirtuins act at least partly through maintenance of genome stability, by sensing and repairing damaged DNA. Sirtuins may also play a role as chromatin regulators in silencing unfavorable gene transcription and regulating metabolic responses to environmental stimuli. Both pch-2 and sir-2 have been closely associated with checkpoint functions and protection of repetitive DNA (rDNA) in yeast. Interestingly, the investigations herein on worm lifespan modulation suggest that pch-2 and sir-2 independently and reciprocally influence lifespan. A plausible mechanism is proposed thatpch-2 interacts with sir-2 in lifespan extension (FIG. 7).

In summary, a novel gene is described that involves lifespan extension in *C. elegans*. This gene effectively extended lifespan in over-expressing lines under a variety of stressors and knockdown of the gene resulted in shortening of lifespan. The mechanism of action of PCH-2 may be similar to the actions of the sirtuin family. Furthermore, the lifespan effects of this gene may also be effective in other animal systems, including in mammalian species.

Example 2

BMK-1 Regulates the Lifespan in *C. elegans* by Activating hsp-16 bmk-1/KIF11 is an evolutionarily conserved gene, and the expression of bmk-1/KIF11 declines with mammalian tissue aging. To understand the evolutionary conservation of the bmk-1 gene, the homology of BMK-1 protein sequences among various species was examined using the NCBI RefSeq database. A phylogenetic analysis was performed using EMBL-EBI Clustal Omega to assess the protein sequence alignment of bmk-1 and its homologs. BMK-1, similar to PCH-2, is an evolutionarily conserved gene with a myosin and kinesin motor domain, which belongs to the P-loop_NTPase family and is found across multiple species, including yeast (*S. cerevisiae*), worm (*C. elegans*), fly (*D. melanogaster*), zebrafish (*D. rerio*), rodent (*R. novegicus, M. musculus*) and human (*H. sapiens*) (FIG. 10A). BMK-1 is critical for the faithful segregation of chromosomes as a mitotic cell cycle and checkpoint regulator. bmk-1 provides an evolutionarily conserved function for both recombination and the formation of more complex chromosome structures. Hence, bmk-1 provides a basic function across the animal kingdom.

To determine the pattern of expression of BMK-1/KIF11 across species and as a function of age, gonadal and brain tissues from mouse and human samples were examined. Expression levels of KIF11 mRNA were measured by Affymetrix array analysis in murine and human specimens. Gene expression was quantified in young subjects: 3-month old mice (N=5) from two aging colonies, C57B/6 and DBA2, as well as in 18-25 year-old humans (male and female, N=8). Aged subjects were also examined: 22-month old mice from two aging colonies (N=5 for each colony), and humans >60 years old (N=10).

The expression of KIFII declined significantly with physiological aging in gonadal and brain tissues of both human and mouse (FIG. 10B). This was assessed by both fold change in mRNA expression, as well as by p values (p<0.01). This observation suggests an evolutionarily conserved loss of expression of the bmk-1 homolog with tissue aging across mammalian species. Based upon these observations, it was determined whether KIF11 plays a role in longevity. Given that lifespan in C. elegans is only 3-4 weeks, as opposed to approximately 2-3 years in mice, the impact of the bmk-1 gene expression on lifespan in *C. elegans* was examined.

Figure 15:
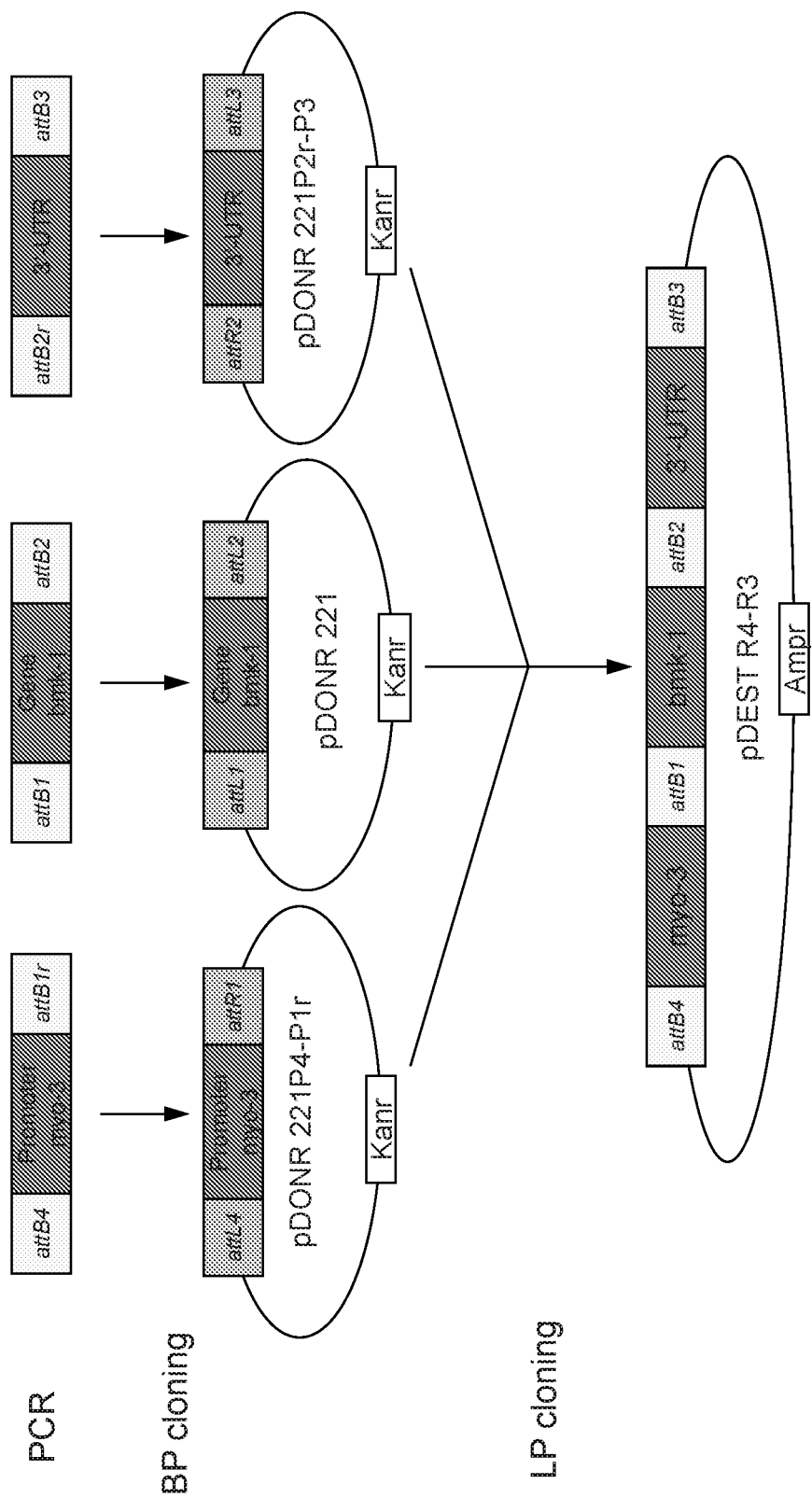
FIG. 15 is an illustration showing the construction of bmk-1 and GFP plasmids.
Figure 16:
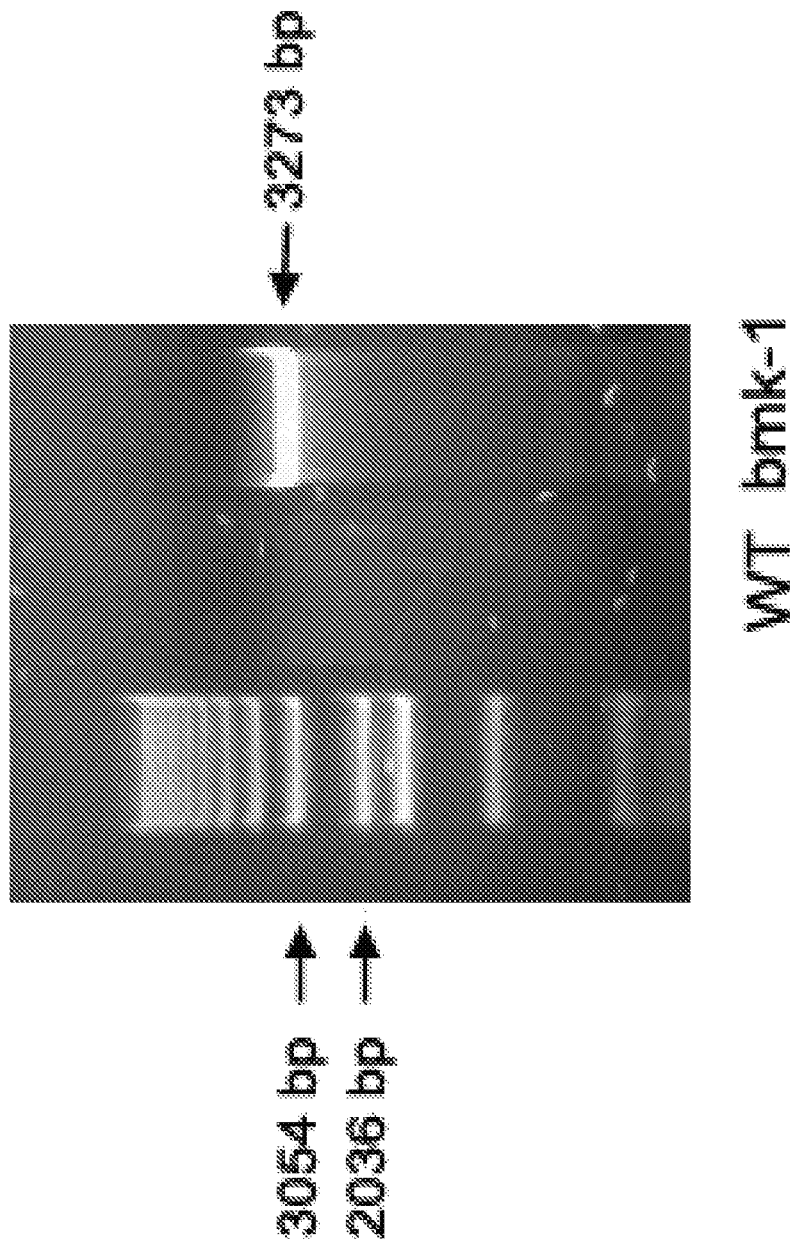
FIG. 16 is an image showing genotyping of bmk-1 shows a band at 3273 bp indicating the transgene in the bmk-1 over-expressing line.

Expression of bmk-1 regulated lifespan of *C. elegans*. *C. elegans* lines over-expressing bmk-1 were generated that co-expressed green fluorescent protein (GFP) by a microinjection method (FIG. 15), and studied the functional impact of bmk-1 on worm longevity. To identify over-expressing bmk-1 lines, animals were selected that co-expressed GFP by direct visualization. In the GFP-expressing lines, the expression levels of bmk-1 were also measured using quantitative reverse transcription polymerase reaction (qRT-PCR). The expression of endogenous and exogenous bmk-1 was determined using an expression vector-specific primer and a bmk-1-specific primer (FIG. 16).

Figure 11:
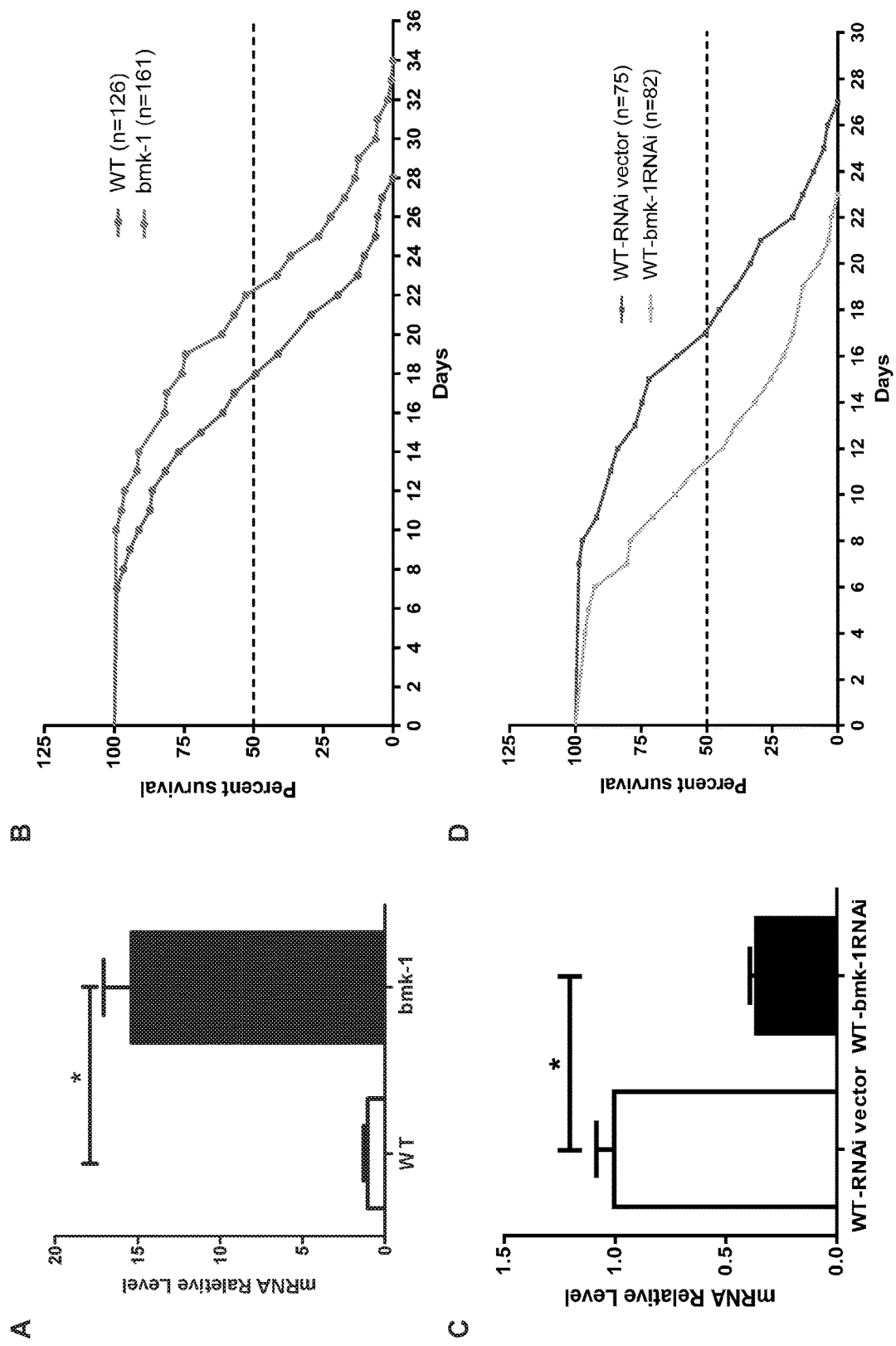
FIG. 11, comprising

In the GFP-positive over-expressing lines, the level of exogenous bmk-1 expression was ten times higher than the level of endogenous bmk-1 in the wild-type (WT, GFP-expressing) controls (FIG. 11A). After confirming over-expression of bmk-1 in worm lines, the Bmk-1 over-expressing worms and WT worms were subjected to lifespan measurements. The median lifespans of WT and bmk-1 over-expressers were 18 days and 22 days, respectively, with maximum lifespans of 28 days and 34 days, respectively (FIG. 11B). Hence, bmk-1 over-expressing lines extended both median and maximum lifespan by approximately 25% as compared to WT (log rank test, N=126/161, p<0.001).

Figure 12:
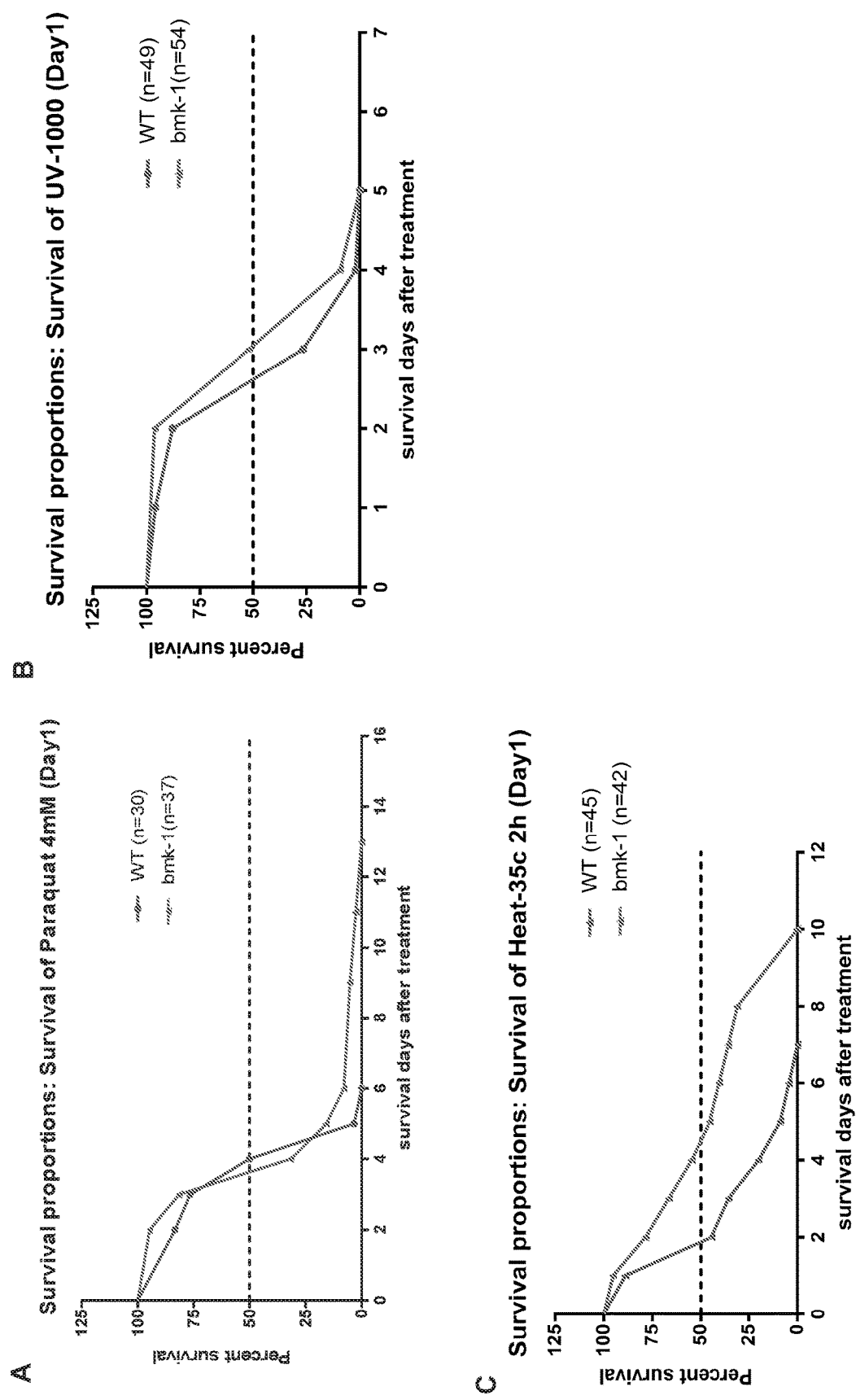
FIG. 12, comprising
Figure 13:
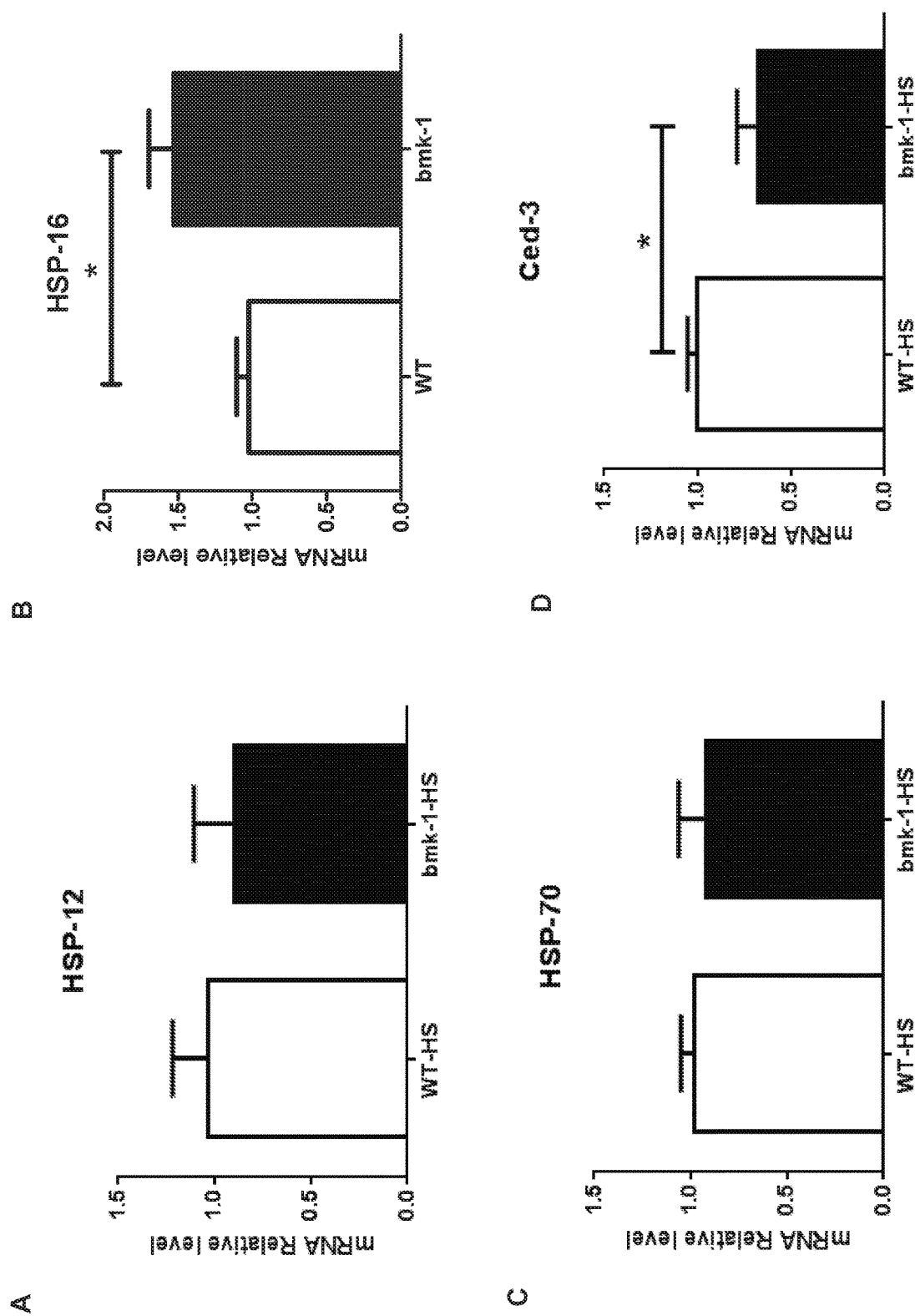
FIG. 13, comprising
Figure 17:
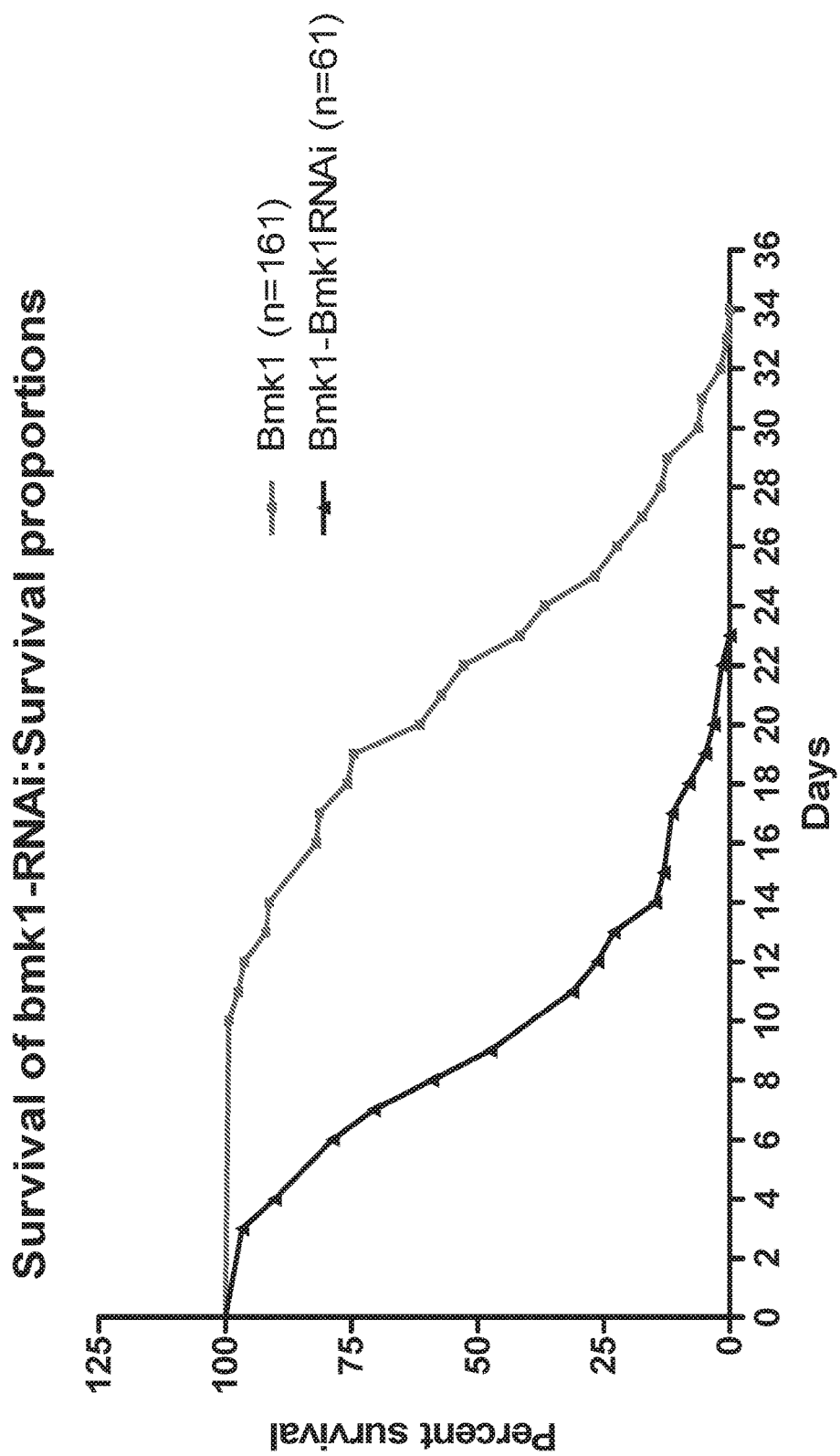
FIG. 17 is a graph showing the shortened lifespan of bmk-1 over-expressing worms after bmk-1 specific RNAi treatment (p<0.0001).

Next, lifespan after RNAi-induced bmk-1 knockdown was examined in WT (without GFP) N2 animals. A bmk-1 specific RNAi clone, F10B5.5, was used to feed WT N2 worms, thereby reducing bmk-1 expression. Only 36% expression levels of bmk-1 remained after bmk-1-RNAi treatment, as assessed by qRT-PCR (FIG. 2C, p<0.01). The median lifespan of WT animals was 17 days, but this was shortened to 11.5 days after bmk-1 RNAi treatment. Maximum lifespan was shortened to 23 days from 27 days, and both median and maximum lifespan were significantly shortened by bmk-1 knockdown (p<0.0001) (FIG. 11D). Similar results were also observed from RNAi inhibition in bmk-1 over-expressing worm lines (FIG. 17).

bmk-1 over-expressing lines have enhanced stress response. Next, it was determined whether bmk-1 over-expressing lines could withstand various stressors better than WT (GFP-expressing) controls. Young adult worms that over-expressed bmk-1 and WT controls were treated with the oxidative stressor, paraquat, at 4 mM for the duration of their lifespan. The median lifespan of bmk-1 over-expressing lines and the control lines were all about 4.0 days. However, the maximum lifespan of bmk-1 over-expressing and WT lines were 13 days and 6 days, respectively, which is an increase of about 120% in maximal lifespan for bmk-1 over-expressors (p<0.001 maximal lifespans as compared to WT controls by log rank test) (FIG. 12A).

Worms were exposed to a DNA damage stressor, UV radiation at 0.1 J/cm$^2$, on day 1. The median lifespan of bmk-1 over-expressing lines was 3.0 days and that of control lines was 2.6 days after UV radiation (20% higher for bmk-1 over-expressers, p<0.01), while the maximum lifespans were 5 days for both (FIG. 12B).

Heat shock was administered at 35° C. for 2 hours, after which animals were removed to routine conditions and their lifespans tallied. Intriguingly, the median lifespan of bmk-1 over-expression lines was 130.0% longer than that of control lines (4.4 days vs. 1.9 days) (p<0.0001), and the maximum lifespan of bmk-1 over-expressing lines was increased by 43% as compared to that of control lines (10 days vs. 7 days) (FIG. 12C). Hence, bmk-1 conferred some lifespan extension in the setting of multiple stressors which affected both DNA and protein integrity, but the response to heat-shock was greater than that observed for the other two stressors, and was highly significant These results imply that bmk-1 enhanced stress-coping capacities in the worm, particularly with regard to heat-shock, and thereby extended lifespan.

hsp-16 is involved in the longevity function of bmk-1 in *C. elegans*. Since bmk-1 over-expression seemed to confer the greatest resistance to heat shock as compared to other stressors tested, the key components of heat-shock proteins and/or apoptosis pathways may be involved in the beneficial survival effect. Therefore, the expression of several well-known heat shock proteins (HSPs) were measured, as well as the cell death molecule in *C. elegans*—ced-3, the core apoptotic cell death executioner, after heat-shock. Among three measured HSPs, hsp-12, hsp-16 and hsp-70, hsp-16 expression was significantly increased in bmk-1 over-expressing lines as compared to control lines, while the expression levels of hsp-12 and hsp-70 were not significantly different (FIGS. 13A-13D). Furthermore, expression of ced-3 was reduced significantly in bmk-1 over-expressing lines under baseline conditions as compared to WT controls (FIGS. 13A-13D). Over-expression of hsp-16 has been reported to extend lifespan in worms, and activation of caspases such as ced-3 is known to promote cell death. The results described herein suggest that the HSP-16 pathway is affected by bmk-1 and may contribute to the observed lifespan extension.

Figure 14:
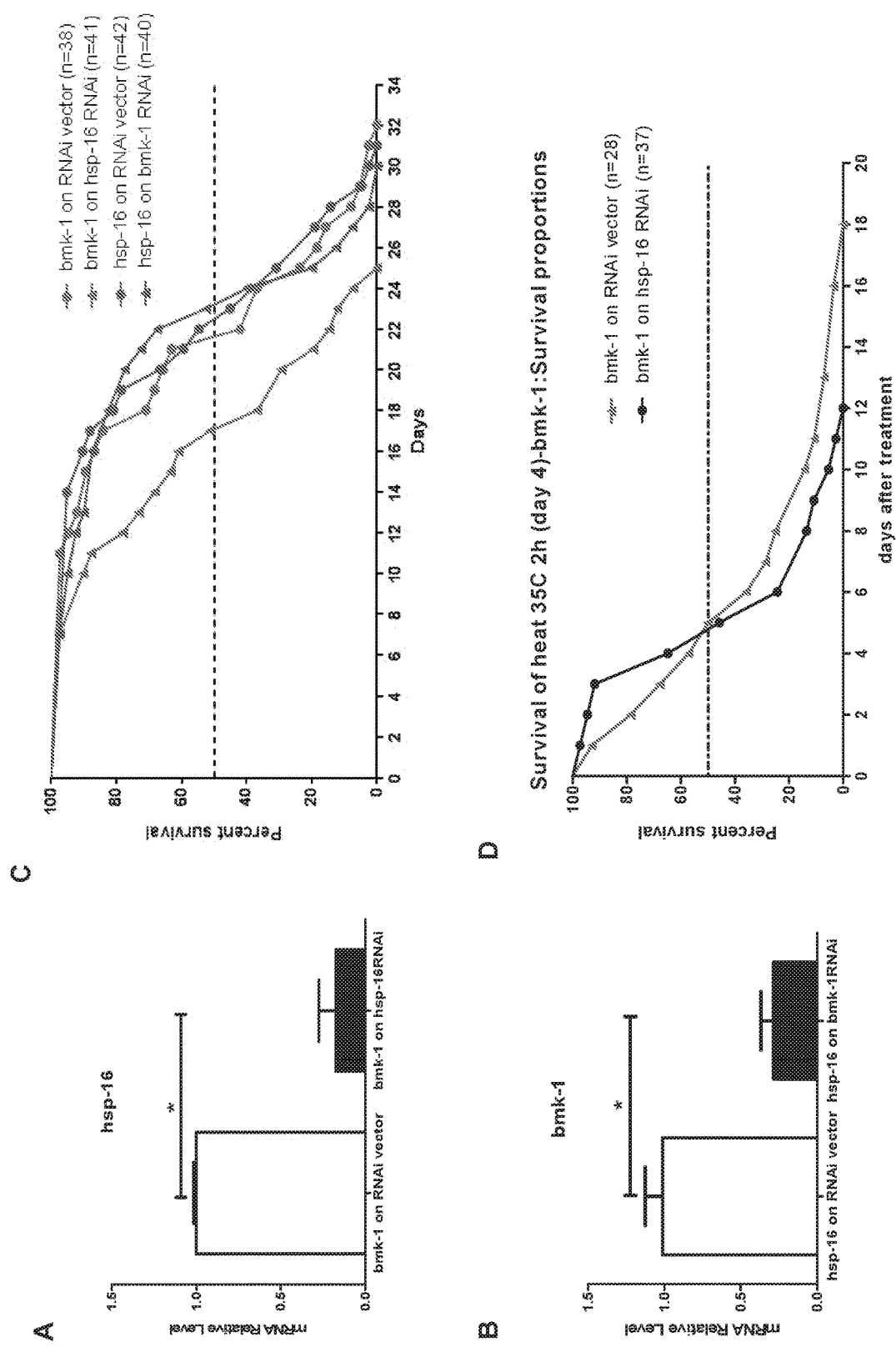
FIG. 14, comprising

To further investigate whether hsp-16 is a key mediator in bmk-1 effects on lifespan, genetic epistasis studies were applied with specific RNAi for hsp-16 in bmk-1 over-expressing worm lines and in bmk-1 in hsp-16 over-expressing lines. First, the effectiveness of hsp-16 RNAi was validated in bmk-1 over-expressing worms. A significantly reduced expression of hsp-16, over 80%, was observed in bmk-1 overexpressors that were exposed to HSP-16 RNAi (FIG. 14A). RNAi treatment specific for bmk-1 in hsp-16 over-expressing worms resulted in a decrease of 70% of expression levels for bmk-1 (FIG. 14B).

The genetic epistasis investigations showed that reducing hsp-16 expression in bmk-1 over-expressing worms significantly decreased both median and maximum lifespans of these animals (77% and 78%, respectively) (p<0.0001). However, reducing bmk-1 expression by RNAi in hsp-16 longevity worms did not change either median or maximum lifespans of hsp-16 worms (FIG. 14C). These results suggest that HSP-16 is essential for BMK-1's lifespan regulation in worms, and may work downstream of BMK-1. In contrast, in animals that already constitutively over-express HSP-16, the bmk-1 knockdown did not affect their lifespan (FIG. 14C).

Lastly, it was determined whether knocking-down hsp-16 by RNAi in bmk-1 over-expressing lines would affect the capacity to cope with stress in this worm line. Heat shock was administered at 35° C. for 2 hours and afterwards animals were removed to routine conditions and their lifespans were tallied. The maximum survival of hsp-16 RNAi treated bmk-1 over-expressing lines was 33% shorter than that of control lines (12 days vs. 18 days) (p<0.0001) (FIG. 14D). This indicates that heat-shock resistance of bmk-1 over-expressing worms was acquired and relied on the expression level of hsp-16 . Taking together, HSP-16 is suggested as a key mediator for BMK-1's lifespan extension function by conferring a significant enhancement of stress-coping ability.

Genes that are essential for development and growth are highly conserved in evolution, and the evolutionary conserved genetic pathways such as insulin/IGF-1 and TOR have been reported to determine normal lifespan in animals ranging from yeast, worm, and fly to rodents. This suggests that both development and aging are essential for survival and evolution in animal kingdom. It is reasonable that some genes may play roles in both development process and aging or lifespan determination. Indeed, a few identified genes are not only crucial for development, but also associated with lifespan determination. In early *C. elegans* embryonic stages, BMK-1 localizes to the region of overlapping interpolar microtubules and functions as a regulator that governs the rate of spindle elongation, as well as the chromosome segregation. The study described herein is the first to suggest that BMK-1 also regulates the lifespan in worms, and that the expression of KIF11, the mammalian homolog of BMK-1, declines with mouse and human tissue aging.

The mechanism by which BMK-1 extends lifespan may be through enhanced expression of hsp-16 and inhibition of ced-3, as suggested by the genetic epistasis study of FIGS. 14A and 14B. It appears that hsp-16 is essential for bmk-1-induced lifespan extension, and also accounts for the enhanced heat shock stress resistance of bmk-1 worms.

Heat shock proteins, also called molecular chaperones, are well-known mediators of stress resistance. A large body of evidence accumulated in senescence models at the cellular and whole animal level has consistently shown that heat shock gene expression, in response to various stressors, is poorly induced in aged subjects. hsp-16 is a small chaperone protein and has been observed to have elevated expression in long-lived worms and transgenic overexpression of hsp-16 in *C. elegans* increased worm life span. These observations have already implicated a link between HSP-16 and lifespan regulation by protecting cells from stress. ced-3, the equivalent of mouse and human caspase-1, is a key regulator that promotes cell apoptosis. The reduction of CED-3 expression in bmk-1 over-expressing worms suggested an inhibition of the cell apoptosis program, which may stem from increased cellular protection in the setting of increased hsp-16, and which may also contribute to a longer lifespan.

As described herein, BMK-1 has a new role in lifespan extension in *C. elegans*. This gene effectively extends lifespan in over-expressing lines under a variety of stressors, and knockdown of the gene results in shortened lifespan. The mechanism of action of BMK-1 is likely mediated by enhancing the expression hsp-16.

Example 3

Overexpression of Human Homologs Improved Viability After Stress

In order to test the impact of over-expression of the TRIP13 and KIF11 genes on the viability of human cells in response to various stressors, retroviral constructs containing each of the two genes were made. Human fibroblasts were then infected with the retroviruses, to over-express either TRIP13 or KIF11, the human homologs of PCH-2 and BMK-1. The over-expressing cell lines were then exposed to various stressors, including oxidative stress (FIG. 18A), etoposide (FIG. 18B), and UV radiation (FIG. 18C). Cell survival after each stress was tallied for wild type (WT) cells, cells infected with only the "empty vector" having no transgene of interest, and then cell lines over-expressing the two transgenes TRIP13 and KIF11. Triplicate experiments were performed, which showed that both TRIP13 and KIF11 over-expression in human fibroblast cells improved viability after both oxidative stress with hydrogen peroxide, and after UV radiation stress of a dose sufficient to cause DNA damage. Cell viability after treatment with etoposide, which induces DNA strand breaks, was improved for both genes over empty-vector and WT controls, but this difference was not statistically significant (FIG. 18B).

Figure 18A:
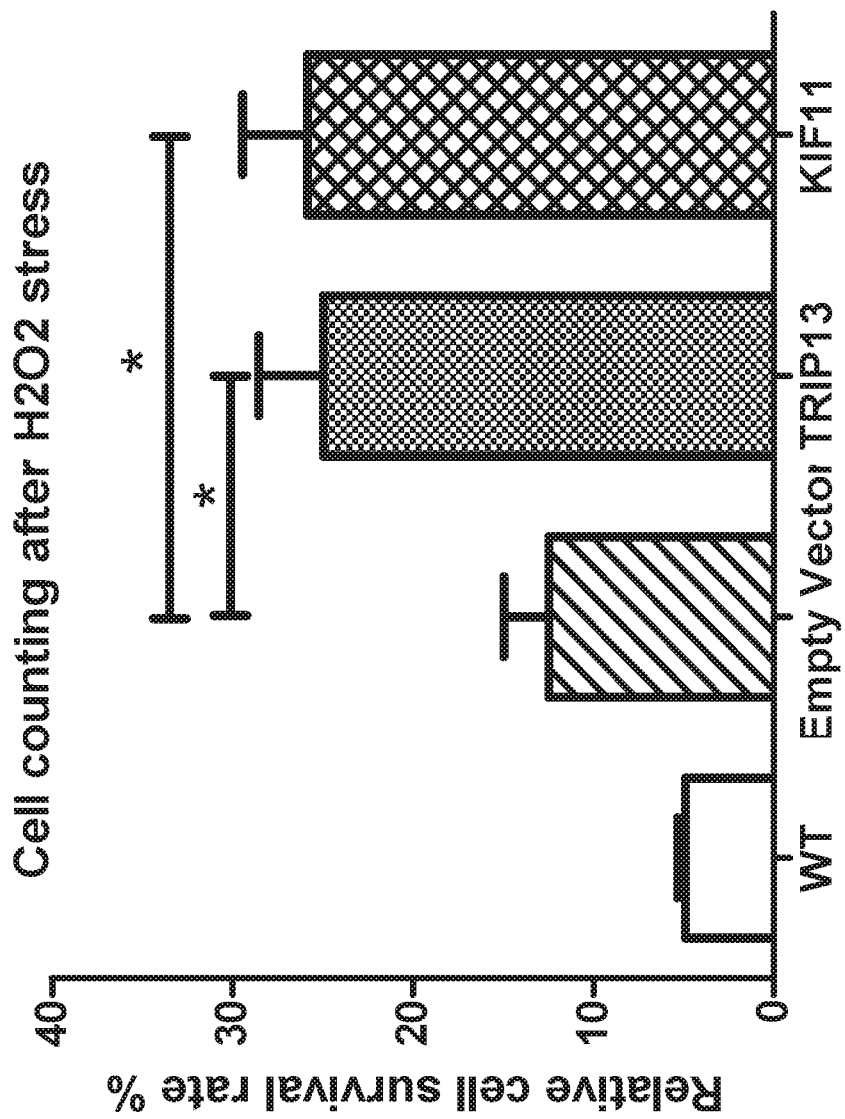
FIG. 18A is a graph showing cell counts of human fibroblasts overexpressing TRIP13 and KIF11 genes after $H_2O_2$ stress.
Figure 18B:
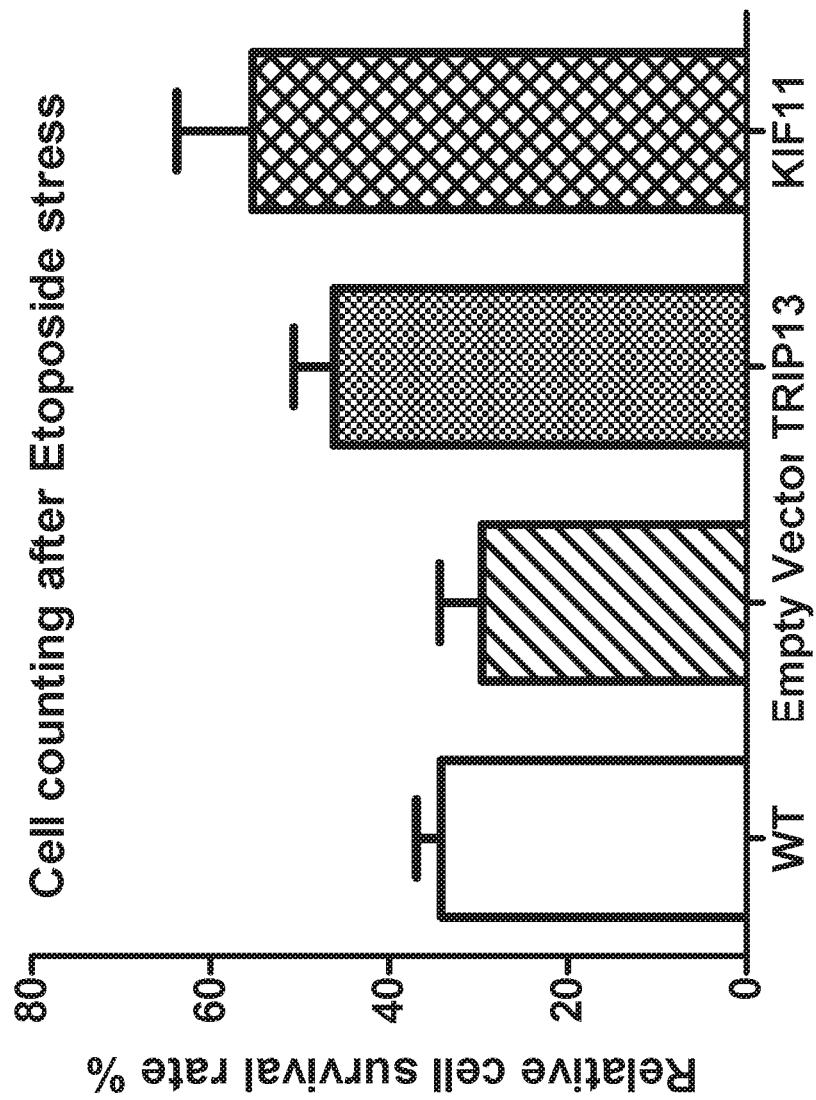
FIG. 18B is a graph showing cell counts of human fibroblasts overexpressing TRIP13 and KIF11 genes after etoposide stress.
Figure 18C:
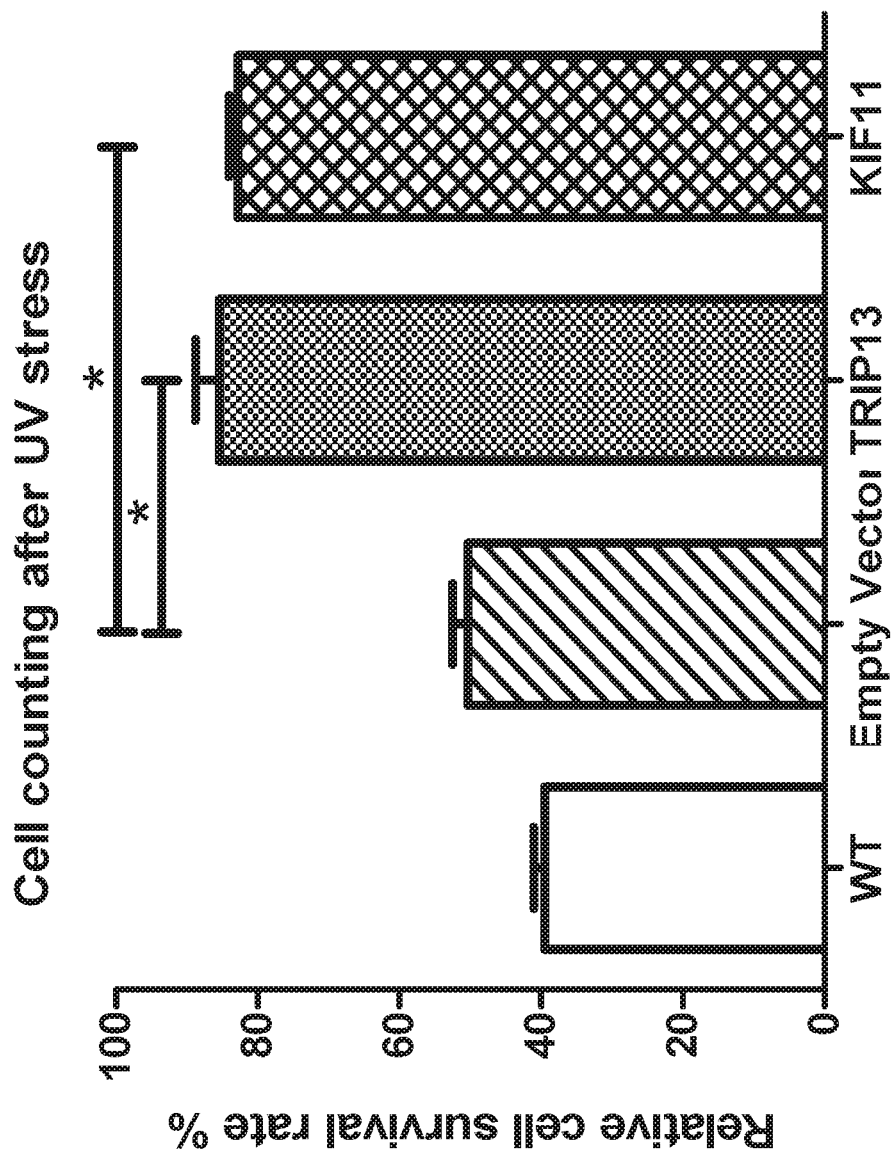
FIG. 18C is a graph showing cell counts of human fibroblasts overexpressing TRIP13 and KIF11 genes after UV radiation, which causes DNA and protein damage, as compared to WT human fibroblasts and human fibroblasts infected with a control vector carrying no transgene of interest.

Results of human fibroblast cells lines over-expressing TRIP13 and KIF11, compared to empty-vector and WT control cell lines, are shown in FIGS. 18A-18C. In each case, cell number was counted after exposure to the stress. For comparisons between the groups, a "*" indicates a statistically significant difference at the p<0.05 level for Student's paired t-test. For both TRIP13 and KIF11, cell survival rate was significantly improved over both empty vector and WT cells after $H_2O_2$ stress and UV stress.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for increasing longevity of a cell or organism comprising administering to the cell or organism a composition that induces expression of at least one homolog selected from the group consisting of Pachytene Checkpoint 2 (PCH-2), BimC subfamily of kinesin-1 (BMK-1), Thyroid receptor-interacting protein 13 (TRIP13) and kinesin family member 11 (KIF11).

2. The method of claim 1, wherein the composition comprises at least one selected from the group consisting of a nucleic acid encoding the homolog and a modulator of the homolog.

3. The method of claim 2, wherein the modulator is selected from the group consisting of an activator of the homolog that increases gene expression of a gene encoding a heat shock protein and an inhibitor of the homolog that decreases expression of a regulator that promotes cell apoptosis.

4. The method of claim 1, wherein the composition increases resistance of the cell to at least one of oxidative stress, apoptosis, heat shock stress, DNA damage, protein damage and aging.

5. A method for increasing cellular resistance to stress, aging or DNA damage in a cell comprising contacting the cell with a composition that induces expression of at least one homolog selected from the group consisting of Pachytene Checkpoint 2 (PCH-2), BimC subfamily of kinesin-1 (BMK-1), Thyroid receptor-interacting protein 13 (TRIP13) and kinesin family member 11 (KIF11).

6. The method of claim 5, wherein the composition comprises at least one selected from the group consisting of a nucleic acid encoding the homolog and a modulator of the homolog.

7. The method of claim 6, wherein the modulator is selected from the group consisting of an activator of the homolog that increases gene expression of a heat shock protein and an inhibitor of the homolog that decreases expression of a regulator that promotes cell apoptosis.

8. The method of claim 5, wherein the composition increases resistance of the cell to at least one of oxidative stress, apoptosis, heat shock stress, DNA damage, protein damage and aging.

9. A method for increasing longevity of a cell or organism comprising administering a composition comprising a homolog selected from the group consisting of Pachytene Checkpoint 2 (PCH-2) and BimC subfamily of kinesin-1 (BMK-1).

10. A method for increasing cellular resistance to stress, aging or DNA damage in a cell comprising contacting the cell with a composition comprising a homolog selected from the group consisting of Pachytene Checkpoint 2 (PCH-2) and BimC subfamily of kinesin-1 (BMK-1).

* * * * *

SEQUENCE LISTING

```
<160> NUMBER OF SEQ ID NOS: 40

<210> SEQ ID NO 1
<211> LENGTH: 23
<212> TYPE: DNA
<213> ORGANISM: Artificial Sequence
<220> FEATURE:
<223> OTHER INFORMATION: Synthetic sequence

<400> SEQUENCE: 1
ctatgaccat gattacgcca agc                                            23

<210> SEQ ID NO 2
<211> LENGTH: 22
<212> TYPE: DNA
<213> ORGANISM: Artificial Sequence
<220> FEATURE:
<223> OTHER INFORMATION: Synthetic sequence

<400> SEQUENCE: 2
gatgatgagg attcacgaca ca                                             22

<210> SEQ ID NO 3
<211> LENGTH: 52
<212> TYPE: DNA
<213> ORGANISM: Artificial Sequence
<220> FEATURE:
<223> OTHER INFORMATION: Synthetic sequence

<400> SEQUENCE: 3
ggggacaagt ttgtacaaaa aagcaggctc gttggattcg acaatggcat cc            52

<210> SEQ ID NO 4
<211> LENGTH: 50
<212> TYPE: DNA
<213> ORGANISM: Artificial Sequence
<220> FEATURE:
<223> OTHER INFORMATION: Synthetic sequence

<400> SEQUENCE: 4
ggggaccact ttgtacaaga aagctgggtc tgtgcgttag ttttcgaaat                50

<210> SEQ ID NO 5
```

```
<211> LENGTH: 46
<212> TYPE: DNA
<213> ORGANISM: Artificial Sequence
<220> FEATURE:
<223> OTHER INFORMATION: Synthetic sequence

<400> SEQUENCE: 5
ggggacaact ttgtatagaa aagttgaacg gctataataa gttctt          46

<210> SEQ ID NO 6
<211> LENGTH: 45
<212> TYPE: DNA
<213> ORGANISM: Artificial Sequence
<220> FEATURE:
<223> OTHER INFORMATION: Synthetic sequence

<400> SEQUENCE: 6
ggggactgct tttttgtaca aacttgttct agatggatct agtgg           45

<210> SEQ ID NO 7
<211> LENGTH: 21
<212> TYPE: DNA
<213> ORGANISM: Artificial Sequence
<220> FEATURE:
<223> OTHER INFORMATION: Synthetic sequence

<400> SEQUENCE: 7
tcaacttgaa tgtggttctc c                                     21

<210> SEQ ID NO 8
<211> LENGTH: 20
<212> TYPE: DNA
<213> ORGANISM: Artificial Sequence
<220> FEATURE:
<223> OTHER INFORMATION: Synthetic sequence

<400> SEQUENCE: 8
caaatttctc ggcgatttgt                                       20

<210> SEQ ID NO 9
<211> LENGTH: 20
<212> TYPE: DNA
<213> ORGANISM: Artificial Sequence
<220> FEATURE:
<223> OTHER INFORMATION: Synthetic sequence

<400> SEQUENCE: 9
cgaaagttgc ggagaatcat                                       20

<210> SEQ ID NO 10
<211> LENGTH: 20
<212> TYPE: DNA
<213> ORGANISM: Artificial Sequence
<220> FEATURE:
<223> OTHER INFORMATION: Synthetic sequence

<400> SEQUENCE: 10
ttcacatcgc aagtctccac                                       20

<210> SEQ ID NO 11
<211> LENGTH: 19
<212> TYPE: DNA
<213> ORGANISM: Artificial Sequence
<220> FEATURE:
<223> OTHER INFORMATION: Synthetic sequence

<400> SEQUENCE: 11
```

-continued ggctcagatg gaacgtcaa                                             19

<210> SEQ ID NO 12
<211> LENGTH: 20
<212> TYPE: DNA
<213> ORGANISM: Artificial Sequence
<220> FEATURE:
<223> OTHER INFORMATION: Synthetic sequence

<400> SEQUENCE: 12
gcttgaactg cgagacattg                                            20

<210> SEQ ID NO 13
<211> LENGTH: 20
<212> TYPE: DNA
<213> ORGANISM: Artificial Sequence
<220> FEATURE:
<223> OTHER INFORMATION: Synthetic sequence

<400> SEQUENCE: 13
cggagttcct gcatttcttc                                            20

<210> SEQ ID NO 14
<211> LENGTH: 20
<212> TYPE: DNA
<213> ORGANISM: Artificial Sequence
<220> FEATURE:
<223> OTHER INFORMATION: Synthetic sequence

<400> SEQUENCE: 14
acagacggct tgaatgaacc                                            20

<210> SEQ ID NO 15
<211> LENGTH: 20
<212> TYPE: DNA
<213> ORGANISM: Artificial Sequence
<220> FEATURE:
<223> OTHER INFORMATION: Synthetic sequence

<400> SEQUENCE: 15
tgaaaaggca cttcgtgatg                                            20

<210> SEQ ID NO 16
<211> LENGTH: 20
<212> TYPE: DNA
<213> ORGANISM: Artificial Sequence
<220> FEATURE:
<223> OTHER INFORMATION: Synthetic sequence

<400> SEQUENCE: 16
ccaaaggcta ctgcttcgtc                                            20

<210> SEQ ID NO 17
<211> LENGTH: 20
<212> TYPE: DNA
<213> ORGANISM: Artificial Sequence
<220> FEATURE:
<223> OTHER INFORMATION: Synthetic sequence

<400> SEQUENCE: 17
gtgatggctg acgaaggaac                                            20

<210> SEQ ID NO 18
<211> LENGTH: 20
<212> TYPE: DNA

```
<213> ORGANISM: Artificial Sequence
<220> FEATURE:
<223> OTHER INFORMATION: Synthetic sequence

<400> SEQUENCE: 18
gggaggaagt tatgggcttc                                                 20

<210> SEQ ID NO 19
<211> LENGTH: 20
<212> TYPE: DNA
<213> ORGANISM: Artificial Sequence
<220> FEATURE:
<223> OTHER INFORMATION: Synthetic sequence

<400> SEQUENCE: 19
tgctgatcgt atgcagaagg                                                 20

<210> SEQ ID NO 20
<211> LENGTH: 20
<212> TYPE: DNA
<213> ORGANISM: Artificial Sequence
<220> FEATURE:
<223> OTHER INFORMATION: Synthetic sequence

<400> SEQUENCE: 20
tagatcctcc gatccagacg                                                 20

<210> SEQ ID NO 21
<211> LENGTH: 35
<212> TYPE: DNA
<213> ORGANISM: Artificial Sequence
<220> FEATURE:
<223> OTHER INFORMATION: Synthetic sequence

<400> SEQUENCE: 21
gtattaagga tcctacgtaa tggacgaggc cgtgg                                35

<210> SEQ ID NO 22
<211> LENGTH: 29
<212> TYPE: DNA
<213> ORGANISM: Artificial Sequence
<220> FEATURE:
<223> OTHER INFORMATION: Synthetic sequence

<400> SEQUENCE: 22
acagggtcga ctcagatgta agctgcaag                                       29

<210> SEQ ID NO 23
<211> LENGTH: 52
<212> TYPE: DNA
<213> ORGANISM: Artificial Sequence
<220> FEATURE:
<223> OTHER INFORMATION: Synthetic sequence

<400> SEQUENCE: 23
ggggacaagt ttgtacaaaa aagcaggctc gttcaccatg agtaaaggag aa             52

<210> SEQ ID NO 24
<211> LENGTH: 53
<212> TYPE: DNA
<213> ORGANISM: Artificial Sequence
<220> FEATURE:
<223> OTHER INFORMATION: Synthetic sequence

<400> SEQUENCE: 24
ggggaccact ttgtacaaga aagctgggtc cagcggccga tgttagttag tta            53
```

<210> SEQ ID NO 25
<211> LENGTH: 52
<212> TYPE: DNA
<213> ORGANISM: Artificial Sequence
<220> FEATURE:
<223> OTHER INFORMATION: Synthetic sequence

<400> SEQUENCE: 25
ggggacaagt ttgtacaaaa aagcaggctc gtcagactaa agtatgcacg ag    52

<210> SEQ ID NO 26
<211> LENGTH: 51
<212> TYPE: DNA
<213> ORGANISM: Artificial Sequence
<220> FEATURE:
<223> OTHER INFORMATION: Synthetic sequence

<400> SEQUENCE: 26
ggggaccact ttgtacaaga aagctgggtc taaaatttaa ttatttctac t    51

<210> SEQ ID NO 27
<211> LENGTH: 46
<212> TYPE: DNA
<213> ORGANISM: Artificial Sequence
<220> FEATURE:
<223> OTHER INFORMATION: Synthetic sequence

<400> SEQUENCE: 27
ggggacaact ttgtatagaa aagttgaacg gctataataa gttctt    46

<210> SEQ ID NO 28
<211> LENGTH: 45
<212> TYPE: DNA
<213> ORGANISM: Artificial Sequence
<220> FEATURE:
<223> OTHER INFORMATION: Synthetic sequence

<400> SEQUENCE: 28
ggggactgct tttttgtaca aacttgttct agatggatct agtgg    45

<210> SEQ ID NO 29
<211> LENGTH: 22
<212> TYPE: DNA
<213> ORGANISM: Artificial Sequence
<220> FEATURE:
<223> OTHER INFORMATION: Synthetic sequence

<400> SEQUENCE: 29
gatgatgagg attcacgaca ca    22

<210> SEQ ID NO 30
<211> LENGTH: 20
<212> TYPE: DNA
<213> ORGANISM: Artificial Sequence
<220> FEATURE:
<223> OTHER INFORMATION: Synthetic sequence

<400> SEQUENCE: 30
caaatttctc ggcgatttgt    20

<210> SEQ ID NO 31
<211> LENGTH: 21
<212> TYPE: DNA
<213> ORGANISM: Artificial Sequence
<220> FEATURE:

<223> OTHER INFORMATION: Synthetic sequence

<400> SEQUENCE: 31
tgtgtaaagc gttagcccag a                                              21

<210> SEQ ID NO 32
<211> LENGTH: 22
<212> TYPE: DNA
<213> ORGANISM: Artificial Sequence
<220> FEATURE:
<223> OTHER INFORMATION: Synthetic sequence

<400> SEQUENCE: 32
gccactttcc gaaaaccact ta                                             22

<210> SEQ ID NO 33
<211> LENGTH: 20
<212> TYPE: DNA
<213> ORGANISM: Artificial Sequence
<220> FEATURE:
<223> OTHER INFORMATION: Synthetic sequence

<400> SEQUENCE: 33
ccactcctcc acctttgacg                                                20

<210> SEQ ID NO 34
<211> LENGTH: 20
<212> TYPE: DNA
<213> ORGANISM: Artificial Sequence
<220> FEATURE:
<223> OTHER INFORMATION: Synthetic sequence

<400> SEQUENCE: 34
catgaggtcc accaccctgt                                                20

<210> SEQ ID NO 35
<211> LENGTH: 20
<212> TYPE: DNA
<213> ORGANISM: Artificial Sequence
<220> FEATURE:
<223> OTHER INFORMATION: Synthetic sequence

<400> SEQUENCE: 35
ggaagccaat ttcgtctgtc                                                20

<210> SEQ ID NO 36
<211> LENGTH: 21
<212> TYPE: DNA
<213> ORGANISM: Artificial Sequence
<220> FEATURE:
<223> OTHER INFORMATION: Synthetic sequence

<400> SEQUENCE: 36
ccccatctct gagttcacaa g                                              21

<210> SEQ ID NO 37
<211> LENGTH: 20
<212> TYPE: DNA
<213> ORGANISM: Artificial Sequence
<220> FEATURE:
<223> OTHER INFORMATION: Synthetic sequence

<400> SEQUENCE: 37
tccgacagca atgttcgata                                                20

```
<210> SEQ ID NO 38
<211> LENGTH: 21
<212> TYPE: DNA
<213> ORGANISM: Artificial Sequence
<220> FEATURE:
<223> OTHER INFORMATION: Synthetic sequence

<400> SEQUENCE: 38
tttcgaagaa gacgaccaga a                                              21

<210> SEQ ID NO 39
<211> LENGTH: 20
<212> TYPE: DNA
<213> ORGANISM: Artificial Sequence
<220> FEATURE:
<223> OTHER INFORMATION: Synthetic sequence

<400> SEQUENCE: 39
tgctgatcgt atgcagaagg                                                20

<210> SEQ ID NO 40
<211> LENGTH: 20
<212> TYPE: DNA
<213> ORGANISM: Artificial Sequence
<220> FEATURE:
<223> OTHER INFORMATION: Synthetic sequence

<400> SEQUENCE: 40
tagatcctcc gatccagacg                                                20
```